(12) United States Patent
Ayangbile et al.

(10) Patent No.: US 10,138,444 B2
(45) Date of Patent: Nov. 27, 2018

(54) BACTERIA AND ENZYMES PRODUCED THEREFROM AND METHODS OF USING SAME

(71) Applicant: Agri-King, Inc., Fulton, IL (US)

(72) Inventors: Gbenga Ayangbile, Fulton, IL (US); Mary Grzemski, Fulton, IL (US); James F. Tobey, Jr., Fulton, IL (US); David Spangler, Fulton, IL (US); Lucas Krueger, Fulton, IL (US)

(73) Assignee: Agri-King, Inc., Fulton, IL (US)

( * ) Notice: Subject to any disclaimer, the term of this patent is extended or adjusted under 35 U.S.C. 154(b) by 43 days.

(21) Appl. No.: 15/262,989

(22) Filed: Sep. 12, 2016

(65) Prior Publication Data

US 2017/0073620 A1    Mar. 16, 2017

Related U.S. Application Data

(60) Provisional application No. 62/218,039, filed on Sep. 14, 2015.

(51) Int. Cl.
| | |
|---|---|
| C12P 21/04 | (2006.01) |
| C12N 9/88 | (2006.01) |
| C12N 9/28 | (2006.01) |
| C12N 9/42 | (2006.01) |
| C11D 3/386 | (2006.01) |
| C12R 1/125 | (2006.01) |
| C12P 5/02 | (2006.01) |
| C12P 3/00 | (2006.01) |
| C12N 1/20 | (2006.01) |
| A61K 35/742 | (2015.01) |
| A23K 10/12 | (2016.01) |
| A23K 10/18 | (2016.01) |
| C02F 3/34 | (2006.01) |
| A23K 20/189 | (2016.01) |
| A23K 50/20 | (2016.01) |
| A23K 50/10 | (2016.01) |
| A23K 50/75 | (2016.01) |
| A23K 50/30 | (2016.01) |
| A23K 50/40 | (2016.01) |
| A23K 50/50 | (2016.01) |
| A23K 30/18 | (2016.01) |
| C02F 103/00 | (2006.01) |

(52) U.S. Cl.
CPC .......... *C11D 3/38645* (2013.01); *A23K 10/12* (2016.05); *A23K 10/18* (2016.05); *A23K 20/189* (2016.05); *A23K 30/18* (2016.05); *A23K 50/10* (2016.05); *A23K 50/20* (2016.05); *A23K 50/30* (2016.05); *A23K 50/40* (2016.05); *A23K 50/50* (2016.05); *A23K 50/75* (2016.05); *A61K 35/742* (2013.01); *C02F 3/34* (2013.01); *C12N 1/20* (2013.01); *C12N 9/2417* (2013.01); *C12N 9/2437* (2013.01); *C12P 3/00* (2013.01); *C12P 5/023* (2013.01); *C12R 1/125* (2013.01); *C12Y 302/01001* (2013.01); *C12Y 302/01004* (2013.01); *C02F 2103/005* (2013.01)

(58) Field of Classification Search
CPC .... A23K 10/18; C11D 3/38645; C12N 11/14; C12P 3/00; C12Y 402/01001
USPC ........................ 435/252.3, 232, 23.2, 254.11
See application file for complete search history.

(56) References Cited

U.S. PATENT DOCUMENTS

| | | |
|---|---|---|
| 8,828,124 B1 | 9/2014 | Mahajan |
| 9,040,271 B2 | 5/2015 | Foody |

FOREIGN PATENT DOCUMENTS

WO    2013167613 A1    11/2013

OTHER PUBLICATIONS

Group, Dr. Edward, "3 Ways to Reduce and Neutralize Flatulence www.globalhealingcenter.com/natural-health/3-ways-to-reduce-and-neutralize-flatulence", Published on May 1, 2013, 2 pages.
McDonald, Peter, "The Biochemistry of Silage" (1981).
Anderson, B.K., et al. "Conservation of Wilted and Unwilted Grass Ensiled in Air-Tight Metal Containers with and Wthout the Addition of Molasses", J.Sci. Fd. Agric. (1970) vol. 21, pp. 235-241.
Anderson, B.K., et al. "Conservation of Herbage of Varying Dry Matter Content in Air-tight Metal Containers with Reference to the Carbohydrate Fraction" J. Sci. Fd. Agric. (1970) vol. 21, pp. 228-234.
Das Neves, et al. "30th Symposium on Biotechnology for Fuels and Chemicals" U.S. Dept. of Energy, Office of the Biomass Program, May 2008, Poster presentation, 1 page.
Lourdes, Maria de, et al. "Gel Electrophoresis for Investigating Enzymes with Biotechnological Application" InTech (2012), pp. 97-110.
Novozymes, "Enzymes at work", brochure, 4th Edition 2013, 76 pages.
Noike, Tatsuya, et al. "Characteristics of Carbohydrate Degradation and the Rate-limiting Step in Anaerobic Digestion" Biotechnology and Bioengineering (1985) vol. XXVII, pp. 1482-1489.
Mahmood, Qaisar, et al. "The Rate-Limiting Step in Anaerobic Digestion in the Presence of Phosphine" Toxicology and Industrial Health (2006) 22: pp. 165-172.
Johnston, David B., et al. "Protease Increases Fermentation Rate and Ethanol Yield in Dry-Grind Ethanol Production" Bioresource Technology (2014) 154: pp. 18-25.

(Continued)

*Primary Examiner* — Tekchand Saidha
*Assistant Examiner* — Mohammad Y Meah
(74) *Attorney, Agent, or Firm* — McKee, Voorhees & Sease, PLC

(57) ABSTRACT

A bacteria referred to here as *Bacillus subtilis* 6A-1 is provided, compositions thereof and processes for use of the bacteria, spores, cells, extracts and enzymes. The compositions which comprise the bacteria, spores, cells, extracts and/or enzymes are capable of degrading polysaccharides. Such compositions are capable of degrading cellulose, including plant-produced cellulose, microcrystalline cellulose and carboxymethyl cellulose. The bacteria produces at least two cellulose-degrading protein fractions. Cellulose degrading activity continues across pH2 to pH13.

23 Claims, 16 Drawing Sheets

Specification includes a Sequence Listing.

(56) References Cited

OTHER PUBLICATIONS

Setlow, Barbara, et al. "Heat Killing of Bacillus Subtilis Spores in Water is Not Due to Oxidative Damage" Applied and Environmental Microbiology (1998) vol. 64, No. 10, pp. 4109-4112.
Ali, Safaa M., et al. "Co-Production of Cellulase and Xylanase Enzymes by Thermophilic Bacillus Subtilis 276NS" International Journal of Biotechnology for Wellness Industries (2013) vol. 2, pp. 65-74.
Barr, Brian, et al. "Identification of Two Functionally Different Classes of Exocellulases" Biochemistry (1996) 35: pp. 586-592.
Beauchemin, K.A., et al. "Evaluation of a Nonstarch Polysaccharidase Feed Enzyme in Dairy Cow Diets" J. Dairy Sci. (2000) 83: pp. 543-553.
Bhat, M.K., et al. "Cellulose Degrading Enzymes and Their Potential Industrial Applications" Biotechnology Advances (1997) vol. 15, No. 3 & 4, pp. 583-620.
Chan, Kwong-Yu, et al. "Studies on Cellulase Production by a Bacillus Subtilis" Antonie Van Leeuwenhoek (1987) 53: pp. 125-136.
Goyal, Varsha, et al. "Parametric Optimization of Cultural Conditions for Carboxymethyl Cellulase Production Using Pretreated Rice Straw by *Bacillus* sp. 313SI under Stationary and Shaking Conditions" Biotechnology Research International, vol. 2014, Article ID 651839, 7 pages.
Deka, Deepmoni, et al. "Enhanced Cellulase Production from Bacillus Subtilis by Optimizing Physical Parameters for Bioethanol Production" ISRN Biotechnology, vol. 2013, Article ID 965310, 11 pages.
Correia, Marcos Jose, et al. "Use of Remazol Blue Dyed Avicel for the Determination of Cellulolytic Activity in Basidiomycetes" Rev. Microbial. vol. 29 (1998) 3 pages.
Medve, Jozsef, "Hydrolysis of Microcyrstalline Cellulose by Cellobiohydrolase I and Endoglucanase II from Trichoderma reesei: Adsorption, Sugar Production Pattern, and Synergism of the Enzymes" Biotechnology and Bioengineering (1998) vol. 59, No. 5, pp. 621-634.
Kung Jr. L., et al. "The Effect of Treating Forages with Fibrolytic Enzymes on its Nutritive Value and Lactation Performance of Dairy Cows" J. Dairy Sci. (2000) 83: pp. 115-122.
Miller, Gail Lorenz, et al. "Use of Dinitrosalicylic Acid Reagent for Determination of Reducing Sugar" Analytical Chemistry (1959) vol. 31, No. 3, pp. 426-428.
Meng, F., et al. "Isolation and Characterization of Bacillus Subtilis Strain BY-3, a Thermophilic and Efficient Cellulase-Producing Bacterium on Untreated Plant Biomass" Letters in Applied Microbiology (2014) 59: pp. 306-312.
Priest, Fergus G. "Isolation and Identification of Aerobic Endospore-Forming Bacteria" Springer Science Business Media (1989), pp. 27-56.
Schulein, Martin, et al. "Enzymatic Properties of Cellulases from Humicola Insolens" Journal of Biotechnology (1997) 57: pp. 71-81.
Ozaki, Katsuya, et al. "Purification and Properties of an Acid Endo-1-4-B-Glucanase from *Bacillus* sp. KSM-330", Journal of General Microbiology (1991) 137: pp. 41-48.
Yi, Jing, et al. "Temporal and Spatial Distribution of Bacillus and Clostridium Histolyticum in Swine Manure Composting by Fluorescent in Siti Hybridization (FISH)", Applied Microbial Biotechnology (2012) 93: pp. 2625-2632.
Cutting, Simon M., et al. "Genetic Analysis" Molecular Biology Methods for Bacillus, John Wiley & Sons (1990) pp. 27-74.
Schaeffer, P., "Sporulation and the Production of Antibiotics, Exoenzymes, and Exotoxins" Bacteriological Reviews (1969) pp. 48-71.
Priest, Fergus G. "Systematics and Ecology of Bacillus", Department of Biological Sciences, Heriot Watt University, Scotland, pp. 3-16.
Khan, Feroz "New Microbial Proteases in Leather and Detergent Industries" Innovative Research in Chemistry (2013) 1:1, pp. 1-6.
Bai, Saraswati, et al. "Cellulase Production by Bacillus Subtilis Isolated from Cow Dung" Archives of Applied Science Research (2012) 4(1) pp. 269-279.
Kim, Yu-Kyoung, et al. "Isolation of Cellulolytic Bacillus Subtilis Strains from Agricultural Environments" ISRN Microbiology, vol. 2012, Article ID 650563, 9 pages.
Gautam, Richa, et al. "Optimization, Purification of Cellulase Produced from Bacillus *Subtilis* Subsp. Inaquosorum Under Solid State Fermentation and Its Potential Applications in Denim Industry" International Journal of Science and Research, (Jun. 2014) vol. 3, Issue 6, pp. 1759-1763.
Ng, Thomas, et al. "Comparison of Extracellular Cellulase Activities of Clostridium Thermocellum LQRI and Trichoderma Reesei QM9414" Applied and Environmental Microbiology, (1981) vol. 42, No. 2, pp. 231-240.
Ito, Susumu, et al. "Alkaline Cellulase for Laundry Detergents: Production by *Bacillus* sp. KSM-635 and Enzymatic Properties", Agric. Biol. Chem. (1989) 53(5), pp. 1275-1281.
Official Publication, Names and Definitions of Feed Ingredients, 9 pages.
Figure 5, Cell Architecture, 1 page.
Sneath, Peter H.A., "Endospore-Forming Gram-Positive Rods and Cocci" Bergey's manual of Systematic Bacteriology, (1986) Section 13, pp. 1104-1139.
Trautmann, Nancy, et al."Compost Microorganisms", Cornell Composting, Science and Engineering, www.compost.css.cornell.edu/microorg.html, (1996) 4 pages.
Coyne, Frederick Philip, et al. "On the Production of Mannitol From Hexoses and Pentoses by a White Species of Aspergillus" Studies in the Biochemistry of Micro-Organisms, From the Division of Biochemistry, London School of Hygiene and Tropical Medicine, University of London (1931), 9 pages.
Plaisance, G.P., et al. "The Mannitol-Producing Organisms in Silage" Journal of Bacteriology, (Dec. 27, 1920) VI, No. 5, pp. 431-443.
Branch, Solomon "Probiotics for Flatulence" LIVESTRONG Foundation, updated Jun. 28, 2015, 3 pages.
Shurson, Dr. Jerry, "Using Distiller's Grains in Livestock and Poultry Feeds" Department of Animal Science, University of Minnesota, 38 pages.
Yin, Li-Jung, et al. "Purification and Characterization of A Cellulase from Bacillus Subtilis YJ1" Journal of Marine Science and Technology (2010) vol. 18, No. 3, pp. 466-471.
Martin, Neal, et al. "Fiber Digestibility and Starch Content of Corn Silage" U.S. Dairy Forage Research Center, USDA, Idaho Alfalfa and Forage Conference, Feb. 26-27, 2008. Published Feb. 26, 2008.

BACTERIA AND ENZYMES PRODUCED THEREFROM AND METHODS OF USING SAME

REFERENCE TO RELATED APPLICATION

This application claims priority to previously filed provisional U.S. application Ser. No. 62/218,039, filed Sep. 14, 2015, the contents of which are incorporated by reference in its entirety.

SEQUENCE LISTING

The instant application contains a Sequence Listing which has been submitted electronically in ASCII format and is hereby incorporated by reference in its entirety. Said ASCII copy, created on Sep. 9, 2016, is named 290001-US_SL.txt and is 5,503,786 bytes in size.

BACKGROUND

Microorganisms which are capable of degrading cellulose are useful in multiple applications, but attempts to provide such microbials have met with limited success. Commercial production of cellulase enzymes which can degrade native vegetative cellulose is most successful using specific types of fungi. However, fungi do not lend themselves to use in products which supply viable enzyme producing-microbes. It is very problematic to harvest spores or propagules of fungi. This makes it more difficult to utilize viable cellulase producing fungi as a seed. The viability of such fungal "seeds" for viable conveyance of fungi is relatively sensitive to environmental conditions like heat, moisture, and desiccation. Bacteria have promise in such uses but applications can be limited due to requirements of specific narrow pH conditions and the like. Accordingly there is a need for new enzyme sources.

SUMMARY

Figure 1:
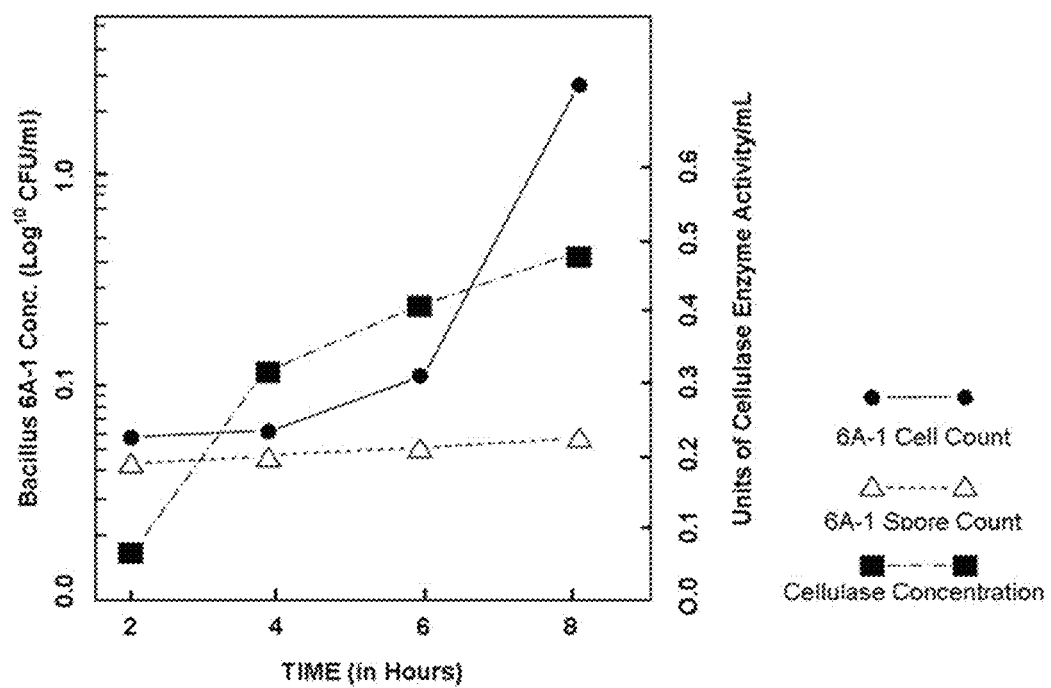
FIG. 1 is a graph showing cellulose production by *Bacillus subtilis* 6A-1. The straight line shows cell count of 6A-1, the dotted line shows spore count and the dashed and dot line shows cellulose concentration.

Described here is a bacterium which comprises the properties of a strain of *Bacillus subtilis* A-1, reference strain having been deposited as ATCC Deposition No. SD-6861. The *bacillus* composition including *Bacillus subtilis* 6A-1 or cells or spores may be used in various fields including, by way of example: ensilage, and the harvesting of feedstuffs, animal feed, as probiotics, ethanol production, waste treatment, and plant growth enhancement. The production of hydrolytic enzymes by *Bacillus subtilis* 6A-1 may be obtained by culturing in mesophilic conditions and in an embodiment using a liquid or semi-solid medium. The strain, spores, cells or extract may be dried, freeze dried, ground, filtered or combined with at least one excipient, carrier or diluent to product a polysaccharide degrading composition. Three enzymatically active protein fractions are produced by the strain and have shown to have activity on plant-produced native (unmodified) cellulose, microcrystalline cellulose and carboxymethyl cellulose. The strain also has protease activity. In an embodiment it is active in degrading the resistant and recalcitrant components of feedstuffs identified as acid detergent fiber (ADF). The strain retains such activity over a pH of 2 to 13. In a further embodiment the enzymes may be extracted, and may be use alone or in combination with the cells, spores or bacteria.

DESCRIPTION

Disclosed here is a unique strain of *bacillus* identified as *Bacillus subtilis* 6A-1 and methods of using same. The strain is capable of degrading polysaccharides. The strain produces three distinct enzymatically active protein fractions which are capable of degrading cellulose. These active protein fractions are separable by polyacrylamide gel electrophoresis. The bacterium can degrade polysaccharides including cellulose and in an embodiment can degrade unmodified, plant-produced cellulose in addition to modified cellulose and microcrystalline cellulose.

A modified cellulose that can be degraded is carboxymethyl cellulose referred to as CMC. Cellulose in the form of CMC readily forms a viscous, colloidal suspension in water, in contrast to crystalline cellulose, and the carboxymethyl groups of CMC are bound to hydroxyl groups of glucopyranose monomers. It is used in food and dairy applications for thickening, water retention and dispersion and chemical stability, for example. It is often used as its sodium salt: sodium carboxymethyl cellulose. The capacity to degrade carboxymethyl cellulose, crystalline cellulose, and cellulose in its natural state is surprising.

Further, it can degrade particularly recalcitrant forms of Acid Detergent Fiber (ADF). This is the least digestible portion of edible parts of the non-grain portion of plants and is what remains after boiling a forage sample in acidic detergent. Components include lignin, cellulose, and insoluble nitrogen and do not include hemicellulose. Methods of measuring ADF are known, such as Van Soest and Wine (1968) "Determination of lignin and cellulose in acid-detergent fiber with permanganate" *J. Assoc. Offic. Anal. Chem.* (AOAC) 51(4) 780-785. (All references cited herein are incorporated herein by reference).

Further, *Bacillus subtilis* 6A-1 can degrade cellulose at a wide range of pH, from pH2 to pH13. The *bacillus* excretes enzymes in extracellular manner which provides for separation and harvesting of these extracellular enzymes where desired. Alternatively, the *bacillus* cells or spores produced by the organism, both cells and spores or a combination of cells and spores and extracted enzymes may be combined for use in various applications. It is shown non-starch polysaccharides are degraded by enzymes produced by the *bacillus*. When used to break down carbohydrates of feed for animals, the result is a more efficient feed conversion providing higher digestible sugar availability and less complex sugars.

*Bacillus subtilis* 6A-1 can be grown in liquid or semi-solid medium, is a mesophile, meaning that the strain has activity, grows, divides, multiplies, and metabolizes best at temperatures below 55° C. These values are not always absolute, but data indicates that 6A-1 does not grow well at temperature 55° C. and above, and certainly it would not be practical to grow the *bacillus* at or above that temperature, and the bacterium can grow and divides in a range of 20° C. to 50° C. with a preferred range of growth at 30° C. to 35° C. These properties provide that *Bacillus subtilis* 6A-1 is useful in a wide range of processes.

*Bacillus subtilis* 6A-1 multiplies and is easily produced in aerobic culture, but is also able to grow under moderately reduced oxygen conditions, often described as being microaerophilic in nature. (Determined by procedure utilizing Brain Heart Infusion Agar (BHIA (L007442) and BD GasPak® systems using BD BBL™ CampyPak™ Plus Microaerophilic System Envelopes with Palladium Catalyst (8801241) for determination. BD Becton, Dickinson and Company Sparks, Md. 21152 US.)

Activity across a broad pH range provides it can be used in many processes which have considerably different pH range requirements, and in processes requiring different pH ranges at different points of the process. The *Bacillus subtilis* 6A-1 may be employed in ensilage fermentation which requires a neutral to alkaline pH at initiation and acidic pH upon completion, as discussed below. When used in feed, the pH may vary from alkaline to acidic throughout the processes of ingestion and digestion. By way of example without limitation, it is useful in processes utilizing degradation of cellulose of plant matter, in ensilage, as an additive to animal or human feed, in waste remediation, and production of biogas. Reference culture of the strain has been deposited with the American Type Culture Collection, ATCC No. SD-6861. A deposit of describe the microorganism is and has been with the American Type Culture Collection (ATCC) Rockville, Md. 20852 USA, ATCC Deposit No SD-6861 The deposit will be maintained in the ATCC depository, which is a public depository, for a period of 30 years or five years after the most recent request, or for the effective life of the patent, whichever is longer, and will be replaced if it becomes nonviable during that period. Additionally, Applicant has satisfied all the requirements of 37 C.F.R. §§ 1.801-1.809, including providing an indication of the viability of the sample. Applicant imposes no restrictions on the availability of the deposited material from the ATCC after issuance of the patent; however, Applicant has no authority to waive any restrictions imposed by law on the transfer of biological material or its transportation in commerce. Applicant does not waive any rights it may have under this patent or any related protection available.

Other enzymes produced by the method described catalyze the degradation of other plant gums and recalcitrant beta-glucans including the beta-linked glucan-polysaccharides of the types represented by lichenin, laminarin, oat spelt, barley and other naturally occurring forages, grasses, and vegetative materials such as wheat straw and corn stover.

As noted the bacteria itself may be used, or the cells or spores or the enzymes it produces. Further, *Bacillus subtilis* 6A-1 also includes asporgenous mutants, that is, bacteria that does not produce spores. Asporogenous mutants of *bacillus* species are well documented (Schaeffer, P. 1969 Sporulation and the Production of Antibiotics, Exoenzymes, and Exotoxins, *Bacteriol. Rev.* 33:48-71). Early-blocked asporogenous mutants will produce less protease and thus increase the amount of cellulolytic enzymes that can be harvested from the mutant of *Bacillus subtilis* 6A-1. Such a mutant strain would be able to produce *Bacillus subtilis* 6A-1 exoenzymes and not produce spores, enabling the separate production of enzymes and spores. The process of induction and isolation of *Bacillus subtilis* 6A-1 may in one embodiment be carried out according to the procedure in Cutting, S. M. and Vander Horn, P. B. (Cutting, S. M. and Vander Horn, P. B. Chapter 2 Genetic Analysis in Molecular Biology Methods for *Bacillus*. Ed Harwood, C. R. and Cutting, S. M. 1990 John Wiley & Sons) presented here by way of example without limitation. A culture of the bacteria is grown in a rich nutrient media at 30° to 39° C. with vigorous aeration until optical density reaches 0.7-1.0. It is then subjected to a mutagen such as ultraviolet light, ethyl methanesulfonate or N-methyl-N-nitro-N-guanidine, nitrous acid and o-methylhydroxylamine. Cells are washed by pelleting the cells by centrifugation and resuspending them in 0.01M phosphate buffered saline twice. An example of a protocol that may be used is as follows. Washed cells are used to inoculate sterile rich nutrient media and grow up overnight at 30° to 39° C. with vigorous aeration. The culture is streaked on sporulating medium agar plates (ie Arret Kirshbaum or Nutrient Sporulating) and incubate overnight at 30° to 39° C. Isolated transparent colonies (opaque and tan colonies are producing spores and can be eliminated from consideration) are picked and used to inoculate a rich nutrient media and incubate overnight at 30° to 39° C. with vigorous aeration. One ml of culture is exposed to 80° C. for one hour then plated on rich media agar plates and incubate overnight at 30° to 39° C. Cultures that are able to grow after heat exposure are not asporgenous and discarded. Remaining cultures are assayed to enzyme production.

Bacilli of various types may be produced and preserved in the following manner presented here by way of example without limitation. The bacteria may be cultivated in either liquid or semi-solid fermentations. In the case of liquid fermentations, viable bacterial cells and spores may be separated and concentrated by filtration of several types including tangential flow filtration and ultrafiltration, or centrifugation, The viable bacterial cells and/or spores may be stabilized by drying or by introduction of stabilizing substances such as propylene glycol, sodium chloride, or other materials that are not toxic to the bacteria but bring about a biostatic state. They also may be subjected to freezing in presence of cryoprotective substances. Drying or desiccation of cells or spores may be accomplished by spray drying, freeze drying, or the introduction of carriers followed by air drying in mobile or static layers or other specialized processes such as fluidized bed drying.

Enzymes produced in liquid fermentation remain in liquid state during downstream processing steps outlined above. The steps above remove the enzyme-producing bacterial cells and/or spores from the liquid. Enzymes in one embodiment may be further concentrated by reverse osmosis or ultrafiltration or they may be precipitated with salts such as ammonium sulfate, the addition of alcohols and nonaqueous solvents, or by other precipitating means. The resultant enzymes, concentrated or unconcentrated, may be dried by spray drying or other methods outlined above, or they may be stabilized in liquid state by the addition of sodium chloride, sucrose, propylene glycol, organic acids, or other biostatic additions which render the enzyme suspension stable and resistant to spoilage.

Enzymes produced via semi-solid fermentation (sometimes called "solid state fermentation" or "koji process") may be extracted by aqueous or non-aqueous solvents and further purified by filtration, centrifugation and concentrated and/or stabilized by the methods taught above. Alternately, enzymes and bacterial cells and spores may be dried together in unseparated state by processes such as simple air drying or fluidized bed drying which preserves both enzyme activity and bacterial cell and spore viability.

The bacteria, spores, cells and/or enzyme products may be further subjected to treating by drying, freezing or filtering as discussed herein or grinding, standardization, or extension with carriers and extenders including, but not limited to: ground limestone and calcium carbonate, sodium chloride, sodium bentonite, zeolites, or other nontoxic mineral compounds or with vegetable or grain or organic products or byproducts such as maltodextrin, dextrose, dried molasses, corn meal or other products, wheat middlings or other products, or even various distillers' by products.

The bacteria, cells, spores or enzymes in an embodiment are combined with a carrier, excipient and/or diluent appropriate for the process in which it will be used. Where administered to an animal, it will be non-toxic to the animal. The carrier, excipient and/or diluent is provided to provide improved properties of the composition, such as standardizing, preserving and stabilizing, allowing the bacteria or component to survived the digestive system of an animal, lubrication, and improve delivery. There are a myriad of such agents available which may be added. Without intending to be limiting, examples include wetting agents and lubricating agents, preservative agents, lipids, stabilizers, solubilizers and emulsifiers such as examples provided below.

Examples of Standardization of the Enzyme Product (Diluent):

Processed Grain By-Products (e.g. brewers dried grains, corn meal, corn gluten meal, ground corn, corn cob fractions, distillers dried grains or solubles, peanut skins, wheat bran, rice bran, rye middlings, wheat middlings and grain sorghum mill feed).

Roughage Products (e.g. ground straw, dried citrus meal, dried beet pulp, almond hulls cottonseed hulls, oat hulls, ground corn cobs, peanut hulls and rice hulls)

Forage Products (e.g. alfalfa leaf meal, ground alfalfa or coastal Bermuda grass hay, ground grass and dehydrated silage).

Molasses Products (e.g. beet, cane or citrus molasses).

Plant Protein Products (e.g. beans, cottonseed meal, peas, soybeans, sunflower meal)

Mineral Products (e.g. calcium carbonate, magnesium mica, diatomaceous earth, bentonites, Zeolites, mineral salts)

Carbohydrate Products (e.g. maltodextrin, starch, cellulose, dextrose, fructose, sucrose, polydextrose, saccharin, powdered or granulated sugar, maltose, sugar alcohols)

Milk and whey products (e.g. dried whey, dried wheyproduct, lactose, dried skimmed milk, dried milk protein, casein, sodium caseinate.

Anti-caking (flow) agents for the enzyme product examples include without limitation: tricalcium phosphate, powdered cellulose, magnesium stearate, sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminium silicate, calcium aluminosilicate, bentonite, aluminum silicate, stearic acid, polydimethylsiloxane.

Examples of preservatives include without limitation sodium chloride, potassium sorbate, calcium or sodium propionate, boric or boronic acid as well as all those "Chemical Preservatives" listed in Section 18 of the *Official Publication* of the Association of American Feed Control Officials, Inc. Champaign, Ill. (2015, 2016).

Emulsifiers and surfactants include without limitation polysorbates (40,60,80), acetylated monoglycerides, monooleates, polyglyceryl fatty acids, e.g. Polyglyceryl-3 Stearate, Polyglyceryl-3 Palmitate, Polyglyceryl-5 Laurate, Polyglyceryl-5; Oleates, Polyglyceryl-10 Diisostearate, Polyglyceryl-3 Polyricinoleate, Glyceryl Oleate, additional polyglyceryl compounds, e.g. Polyglyceryl-6 Caprylate, Polyglyceryl-10 Laurate.

The following is provided as examples of processes in which the strain and products produced may be used without intending to be limiting.

Silage and Animal Feed

Digestion of cellulosic fiber and vegetable gum-type polysaccharides (non-starch polysaccharides—NSPs) represent continuing challenges in various industries. NSPs represent the primary class of incompletely digested feedstuff components in the area of animal feeding. NSPs may also represent anti-nutritional challenges in the practice of animal feeding. These compounds result in changes in intestinal mobility and lower efficiency of production. Even though ruminant-type animals can digest much fiber, the more resistant NSPs and poor quality fiber represent appreciable challenges to complete digestion and most efficient use of feedstuffs. In addition to harvested crops, naturally high in fiber and less digestible, there are great quantities of byproducts of fuel ethanol production and other fibrous products which find their way into animal feeds. These byproducts contain difficult-to-digest substances, but represent potentially valuable feedstuffs if they can be digested and assimilated by animals (See Shurson, J. "Using Distiller's Grains By-products in Livestock and Poultry Feeds," University of MN world widewebbiofuelscoproducts.umn.edu/sites/bio-dieselfeeds.cfans.umn.edu/files/cfans asset 413198.pdf). Distiller's Dried Grains (DDG's) are the dried residue remaining after the starch fraction of corn is fermented with selected yeasts and enzymes to produce ethanol and carbon dioxide. After complete fermentation, the alcohol is removed by distillation and the remaining fermentation residues are produced including wet distiller's grains, condensed distillers solubles, and modified wet distillers grains, which are fed to ruminants, or the condensed distiller's solubles is combined with the wet distiller's grains fraction and dried to produce DDGS. Of all of these co-products, DDGS is the predominant form produced and available to the global feed industry (Shurson, J). Similar grain byproducts are available from the brewing of beer or ales of various types.

Successful ensiling processes depend upon a significant level of fermentable sugar that can be converted to organic acid. Ensiled crops such as legumes, small grains, and various temperate and tropical grasses have relatively high fiber and NSP content and may contain little fermentable sugars. The fermentable sugars are converted to volatile and non-volatile fatty acids by organic acid-producing bacteria. These bacteria require relatively simple sugars. The fatty acids that the aforementioned bacteria produce reduce the overall pH of the ensiled material and preserve it for use as needed. It is essential for preservation that ensiled materials contain a sufficient level of fermentable sugars so that a reasonable preservation rate may be attained. Poorly digestible fiber very often deleteriously affects silage preservation and its feeding quality. (See Martin, et al—Neal Martin, David Mertens, and Mary Beth Hall, "Fiber Digestibility and Starch Content of Corn Silage," U.S. Dairy Forage Research Center, USDA-ARS, 1925 Linden Dr. West, Madison, Wis. 53706, Joe Lauer, U of Wisconsin-Madison. Idaho Alfalfa and Forage Conference, 26-27 Feb. 2008.)

Purified enzymes (like cellulases and other beta-glucanases) have been applied to silage to improve the ensiling process and to livestock and poultry feeds to enable animals to render better feed efficiency from available diets. These enzymes, while they may be cost effective, may also be relatively expensive, are heat labile, and may not have optimal activity in the pH range of the specific feed application. Enzymes also do not reproduce and multiply their effects. Once degraded or denatured, their activity is lost.

Bacteria can be used as components of preparations which contain viable microorganisms which are then fed to animals. Bacteria are fed to many diverse animal species including many species of mammals, avian species, crustaceans and fish. Specific supplements and fermented foods contain bacteria which are consumed by humans. The viable microbial preparations that are fed to animals and humans are known as Probiotics or Direct Fed Microbials (DFMs). They are fed to the aforementioned animal species for such broad ranging effects as increasing feed conversion for more efficient production of milk, of animal protein, eggs, etc. They are also associated with increased resistance to intestinal counter-productive microorganisms and pathogens. They are said to increase positive effects from enzyme production in the gut. In ruminant species particularly, there are other positive effects which have been noted: increased fatty acid production, which often translates into more butterfat in milk; suppression of pathogenic bacteria in the rumen and gut which translates into reduced deleterious microbial load at point of slaughter; increased levels of bypass protein; decreased acidosis, etc.

The attempt to provide cellulase-producing DFMs or viable microbial seed products to the various processes and industries that could utilize the catalytic action of such microbes has had limited success.

DFMs and Probiotics are fed to help minimize negative digestive effects of ingesting feed or foodstuffs that are relatively hard for the animal or human to digest. An often-claimed result of ingesting feedstuffs or foods with indigestible fiber and NSPs are flatulence and other serious anti-nutritional effects (See "Probiotics for Flatulence" http://world wide web.livestrong.com/article/274832-probiotics-for-flatulence/; http://world wide web.globalhealingcenter.com/natural-health/3-ways-to-reduce-and-neutralize-flatulence/Flatulence in dogs: "Dietary causes are the main source of flatulence in dogs. Low-quality foods with ingredients that can't be fully digested can cause gas": at pets.webmd.com/dogs/flatulence-dogs) which is reduced by in ingestion of the compositions described here.

Current supported uses in feed by AAFCO/FDA include NSP-digesting enzymes like those which can hydrolyze xylans, hemicelluloses and beta-glucans. These enzymes are recognized for their effects in reducing "sticky droppings," reducing the viscosity of digesta, and assisting with other anti-nutritional effects in animals (AFCO *Official Publication*).

Septic Tank Application for Bacteria and Enzymes

Enzymes and bacteria are commonly added to septic tanks and other types of waste treatment systems such as cesspools, lagoons, drip systems, composting toilets, sewage systems, wet wells, and camp toilets. These viable bacteria and active enzymes are added in order to more effectively degrade waste and digest solid materials. Some of the most problematic classes of compounds to digest are cellulose, natural fiber, and NSPs. Purified cellulase enzymes may be added to such systems. However, the discovery of bacteria which can produce fiber-digesting enzymes and which can be produced in stable preparations has proven problematic Composting Composting is primarily an aerobic degradative process which helps to stabilize and reduce solid waste, rendering it stable, and producing an organic product which can be used as a mulch, bedding, soil conditioning, or organically-based fertilizing material. The organic waste commonly subjected to the composting process includes paper waste, lignocellulosic materials from agricultural crop production or industrial processes, and solid waste from animals (often confined and concentrated) and additionally from human sewage solids. The moist, undried waste material is piled in heaps or long piles called windrows. The material is turned and mixed regularly, generally with the aid of some type of mechanical equipment to reaerate the piles and to re-expose waste substrates to the multiplying and metabolizing microorganisms residing therein. The greatest portion of this waste is comprised of fiber containing cellulose-based materials. One of the primary purposes of composting is reduce the volume of the waste. Increased cellulosic digestion increases the rate of reduction. The initial stages of composting are considered mesophilic and the primary microbial populations at the stage are said to be bacilli (Trautmann and Olynciw, Yi et al. "Compost Microorganisms" http://compost.css.cornell.edu/microorg.html). The addition of bacteria-containing products is used to accelerate the initial composting activity and sometimes to affect the quality of the end product.

BioGas Production

BioGas is gaseous fuel, especially methane and in some cases, carbon monoxide and hydrogen, produced by the fermentation of organic matter. It includes any gas fuel derived from the decay of organic matter, as the mixture of methane and carbon dioxide produced by the bacterial decomposition of sewage, manure, garbage, or plant crops. Biogas production is a technology which is utilized in various parts of the world, including the US, to digest waste under (primarily) anaerobic conditions and in so doing create appreciable quantities of methane gas which can be used as a fuel source. The efficient production of methane and high energy gas from biological processes requires efficient digestive steps. The initial digestion step depends upon efficient breakdown of fibrous material including the digestion of cellulose and NSPs to alternative substrates with lower molecular weight. The methanogens (bacteria that produce methane) can readily absorb and metabolize these materials with low molecular weight.

It has been stated that the rate limiting step to methanogenesis is the effective degradation of complex polysaccharides such as cellulose and other NSP's into simpler, lower molecular weight compounds. The rate limiting step in methanogenesis (biogas production) is in the first hydrolytic stage of substrate breakdown. The hydrolytic process and the bacteria associated with it (like 6A-1) enzymatically reduce large molecules (like cellulose) to small ones, upon which the biogas process feeds. The following article states that " . . . the hydrolysis of cellulose was so low that this was shown to be the rate-limiting step in overall anaerobic digestion." See Noike et al. (1985) "Characteristics of carbohydrate degradation and the rate-limiting step in anaerobic digestion." *Biotechnol. Bioeng.* 27(10):1482-9; Mahmood et al. (2006) "The rate-limiting step in anaerobic digestion in the presence of phosphine." *Toxicology and Industrial Health* 22(4):165-72. Das Neves, et al. teaches that biogas production can be positively affected by *Bacillus subtilis* and other bacilli-application. Das Neves, Luiz Carlos Martins, et al. "Biogas production by *Bacillus* sp. anaerobic cultivations: new trend of alternative energy source in urbanized areas." Poster presentation. U.S. Department of Energy and Society for Industrial Microbiology special conference "30$^{th}$ Symposium on Biotechnology for Fuels and Chemicals. New Orleans, La. May, 2008.

By way of example, biogas can be formed by transformation of organic material such as plants, most typically crop residue, food and also farm waste such as animal manure, and can even be used to convert human waste to energy. In this instance the bacteria strain or spore or cells or enzyme fraction or all or any of these entities in combination is placed in contact with the organic material or cellulose composition under anaerobic conditions to produce biogas which may include methane, carbon dioxide, nitrogen and possibly also hydrogen sulfide, carbon monoxide and water vapor.

Data on *Bacillus subtilis* 6A-1 indicates that it can grow under conditions of low oxygen content (or microaerophillic conditions). See the methodology and information regarding growing conditions discussed above. Since *bacillus* spores are dormant as far as metabolism is concerned, and very resistant to anaerobic conditions, they can be grown aerobically, or semi aerobically and are well known to be still quite stable, that is retain their potential viability, under anaerobic conditions once they are in spore state. Production of enzymes by *Bacillus subtilis* 6A-1 does not require an aerobic or anaerobic environment. See Sonenshein, et. al. *Bacillus subtilis and Its Closest Relatives from Genes to Cells*. ASM Press, 2002. p. 30 for the lifecycle of *Bacillus subtilis* showing the vegetative cell/spore cycle development.

Furthermore, Barbara Setlow and Peter Setlow "Heat Killing of *Bacillus subtilis* Spores in Water Is Not Due to Oxidative Damage" in *Appl. Environ. Microbiol.* October 1998 vol. 64 no. 10. 4109-4112 state "The heat resistance of wild-type spores of *Bacillus subtilis* or spores (termed α$^-$ β−) lacking DNA protective α/β-type small, acid-soluble spore proteins was not altered by anaerobiosis"

The biogas so produced may be collected by any various methods, and can be subject to further purification or commercial processes. Numerous treatments are available for increasing the volume and efficiency of biogas, some by bacteria addition and some via enzyme addition, the enzymes used are notably cellulase and other NSP digesting catalysts. Without intending to be limiting, such processes available include those described at U.S. Pat. No. 8,828,124 and U.S. Pat. No. 9,040,271 incorporated herein by reference.

Agriculture/Bioag Use

Mixtures of microorganisms are applied to seeds of crops and introduced directly into the soil for the purpose of stimulating and enhancing the growth of crops. Crops can benefit from the introduction of degradative microorganisms into the root zone; those microbes can degrade complex compounds and mineral-binding polymers. The release of nutrients in the root zone results in greater growth and production rates by key crops and other plants. The microbially enhanced biochemical process also results in conservation of key nutrients and prevents the need for over fertilization. Naturally occurring *Bacillus* spp. are considered to be allowable for (certified) organic food production by the U.S. NOP (National Organic Program).

As early as 1993, it was stated that it was beginning to become clear that the well-recognized association of bacilli with roots and seeds might not be just a chance association, and early strategies developed toward the use of bacterial inoculants to improve plant performance. (F. G. Priest, "Systematics and Ecology of *Bacillus*," in Sonenshein et. al. *Bacillus subtilis and other gram positive bacteria*, ASM Press, 1993. p. 12) Furthermore, *Bacillus* species—or other closely related bacterial-strains and genera are desirable for use in food crops, and in agriculture. The use of *Bacillus subtilis* and many more similar strains of bacilli are desirable since those chosen species of bacteria are considered safe, effective, stable and are relatively inexpensive to produce.

Bacilli such as *Bacillus subtilis, Bacillus licheniformis, Lysinibacillus* spp. and *Paenibacillus* spp, are used in some microbial/fertilizer or plant application products for the purpose of enhancing plant food's effects. Some strains are used as registered pesticides and as antagonists to reduce the incidence of (primarily) harmful fungi which attack the seeds or plants.

Detergent or Cleaning Application

Commercially available cellulases for cleaning are generally of the exo-acting cellulase type which catalyze the hydrolysis of crystalline or "native" cellulose, like fibers from cotton. Cellulase enzymes for these applications have been traditionally derived from fungi. Fungal strains include *Trichoderma longibrachiatum/viride/reesei, Aspergillus niger/aculeatus,* and *Humicola insolens. Humicola insolens* genes are cloned into production strains of *A. oryzae* or *A. niger* for practical production of the alkaliphilic *H. insolens'* cellulase. Cellulose-digesting enzymes suitable for detergent and other commercial applications have been more difficult to find in bacteria.

Commercial cellulases are useful in biopolishing of newly manufactured textiles, for providing an abraded or worn look of cellulosic fabric (which term includes cloth, textiles or garment)—especially denim (often called "stone washing"). Suitability for most detergent applications requires that a cellulase be active in the alkaline range, pH 10.0-12.0. Enzymatic cleaning and detergent care use is also discussed at, for example, Lilley et al., "Care Enzymes System" WO 2013167613 A1 incorporated herein by reference. Cellulase may be used for (1) the surface cleaning of microfibrils and micro-pills which occur on cotton or other cellulose-based fabrics and (2) the softening and decolorization of denim material, particularly providing a pre-washed, softened, or pre-worn appearance to denim jeans, including certain cellulases in presoaks or detergents can reduce and remove microfibrils/micro-pills and fray and surface balling on the fabric and enhance the appearance of cotton goods. In still another example, the use of cellulase preparations with or without stones or other physical abrasion additives accelerate the softening and pre-worn look and feel of denim goods. Even further examples relate to textile enzymes to improve production methods and fabric finishing, such as using amylases to remove starch size, cleaning fabric to remove waxes, hemicelluloses and other impurities, removing pectin, or even use with or without stones to achieve a desired appearance of the fabric. Enzymes are useful for a variety of processes to modify fabrics. For examples, see world wide web.novozymes.com/en/about-us/brochures/Documents/Enzymes_at_work.pdf.

The myriad of other potential applications to which the bacterial and cells or spores or enzymes may be used include, by way of example without limitation, deinking and modification of forest products, particularly paper products and use of xylanases (which *Bacillus subtilis* 6A-1 produces) in bleaching paper, with reduction of the use of harsh chemicals.

These are but a few examples use of the 6A-1 enzymes in a composition for conditioning or modifying fabric, where the enzymes are used in a process in which a property of the fabric such as color, texture, wettability or the like is different after application of the enzyme.

Regardless of the specific application, cellulose in fibrous or crystalline form is difficult to digest enzymatically. Although this crystalline cellulose is a beta-glucan by definition, commonly available beta-1,4-glucanases are not effective in hydrolyzing crystalline cellulose. The beta-1,4 glucanases commonly produce by bacilli are more effective against modified cellulose, such as caboxymethylcellulose (CMC), and other beta-glucans (gums) from vegetative origin.

The term plant or plant material or plant part is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. Any plant in which it is desired to break down cellulose may be used in the processes here. By a "crop plant" is intended any plant that is cultivated for the purpose of producing plant material that is sought after by man for either oral consumption, or for utilization in an industrial, pharmaceutical, or commercial process. The compositions may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses.

In referring to a "cellulose-degrading enzyme" is intended an enzyme, including but not limited to cellulases and other glucosidases that can be utilized to catalyze the hydrolysis of or promote the degradation of cellulose into sugar monomers or cellodextrins or smaller molecular weight parts of which the cellulose is composed.

The International Union of Biochemistry (I.U.B.) Hydrolase Enzyme Classification 3.2.1.x includes cellulose degrading enzymes. Listed below, by way of example without intending to be limiting, are several of these I.U.B. classified cellulases.

EC 3.2.1.4 cellulase
EC 3.2.1.6 endo-1,3(4)-β-glucanase
EC 3.2.1.21 β-glucosidase
EC 3.2.1.39 glucan endo-1,3-β-D-glucosidase
EC 3.2.1.58 glucan 1,3-β-glucosidase
EC 3.2.1.91 cellulose 1,4-β-cellobiosidase
EC 3.2.1.136 glucuronoarabinoxylan endo-1,4-β-xylanase
EC 3.2.1.156 oligosaccharide reducing-end xylanase For the degradation of cellulose, for example, two general types of cellulase enzymes can be employed. Cellulase enzymes which cleave the cellulose chain internally are referred to as endo-β-1,4-glucanases (E.C. 3.2.1.4) and serve to provide new reducing and non-reducing chain termini on which exo-β-1,4-glucanases (cellobiohydrolase, CBH; E.C. 3.2.1.91) can operate (Tomme et al. (1995) Cellulose hydrolysis by bacteria and fungi, *Advances in Microbial Physiology* 37:1-81). Two types of exoglucanase have been described that differ in their approach to the cellulose chain. One type attacks the non-reducing end and the other attacks the reducing end. The product of the exoglucanase reaction is typically cellobiose, so a third activity, β-D-glucosidase (E.C. 3.2.1.21), is required to cleave cellobiose to glucose. The exoglucanase can also yield longer glucose chains (up to 6 glucose units) that will require a β-D-glucosidase activity to reduce their size. Relative to the other enzyme activities needed for degradation of cellulose into fermentable sugars, only a minor amount of the β-D-glucosidase activity is required.

The method and compositions described are useful in animals including, but not limited to, humans, canine (e.g., dogs), feline (e.g., cats); equine (e.g., horses), bovine (e.g., cattle), ovine (e.g. sheep), caprine (e.g. goat) porcine animals (e.g., pigs) and rabbit, as well as in avians including, but not limited to, chickens, turkeys, ducks, geese, a quail, a pheasant, parrots, finches, hawks, crows and ratites (ostrich, emu, cassowary, and the like as well as domestic fur animals such as ferrets, minks, mustilids, and fish such as fin-fish, shellfish, and other aquatic animals. Fin-fish include all vertebrate fish, which may be bony or cartilaginous fish. Further examples of fin-fish include salmonid fish, including salmon and trout species, such as coho salmon (*Oncorhynchus kisutch*), brook trout (*Salvelinus fontinalis*), brown trout (*Salmo trutta*), chinook salmon (*Oncorhynchus tshawytscha*), masu salmon (*Oncorhyncus masou*), pink salmon (*Oncorhynchus gorbuscha*), rainbow trout (*Oncorhynchus mykiss*), Arctic charr (*Salvelinus alpinus*) and Atlantic salmon (*Salmo salar*). However, any other fish species may benefit, such as ornamental fish species, koi, goldfish, carp, catfish, yellowtail, sea bream, sea bass, pike, halibut, haddock, tilapia, turbot, wolffish, and so on. Examples of shellfish include, but are not limited to clams, lobster, shrimp, crab and oysters. Other cultured aquatic animals include, but are not limited to eels, squid and octopi. Still further examples include, crustacean (e.g. lobsters, crabs, shrimp, crayfish), mollusks (e.g., squid, clams, octopus, snails, abalone, mussels), Porifera (sponges), Cnidaria (e.g., jellyfish, sea anemones), Ctenophora, Echinodermata and aquatic worms.

The compositions and processes may be particularly useful with ruminant animals. As used here, the term "ruminant" means an even-toed hoofed animal which has a complex 3- or 4-chamber stomach and which typically rechews what it has previously swallowed. Some non-exhaustive examples of ruminants include cattle, sheep, goats, oxen, musk oxen, llamas, alpacas, guanacos, deer, bison, antelopes, camels, and giraffes.

The bacterial cells, spores or enzymes in an embodiment are combined with a carrier, excipient and/or diluent appropriate for the process in which it will be used, as described above. Where administered to an animal, it will be non-toxic to the animal. There are a myriad of such agents available which may be added. Without intending to be limiting, examples include standardizing agents, extenders, wetting agents and lubricating agents, preservative agents, lipids, stabilizers, solubilizers, free flowing agents, and emulsifiers.

Examples that may be particularly useful in administration to an animal include ground corn cobs, salt, ground limestone, calcium carbonate, sodium bentonite, zeolites, ground soy hulls, citrus pulp, dairy byproducts, animal protein products, grain products, plant protein products, processed grain products and by-products, roughage products, molasses products fermentation byproducts such as dried distillers grains and/or solubles, citric acid and glutamic acid fermentation byproducts and the like.

*Bacillus subtilis* 6A-1 produces proteases capable of degrading proteins across a wide range pH, from pH 2 to pH 12. The proteases are excreted in extracellular manner which provides for separation and harvesting of these extracellular proteases where desired. Proteases from *Bacillus subtilis* 6A-1 have many possible applications. Addition of proteases to silage and animal feed yields greater feed efficiencies by rendering the feed more easily absorbed by livestock. Detergents both domestic and industrial have long contained proteases that aid in the removal of proteineous materials. *Bacillus subtilis* 6A-1 protease is able to breakdown keratin a major component of hair and feathers, making it useful for poultry waste treatment and dehairing of hides to prepare leather (See Kahn, F. 2013 "New Microbial Proteases in Leather and Detergent Industries" *Innov. Res. Chem.* 1(1): 1-6). Use of proteases in leathering processes eliminate some of the toxic chemicals and allow for the simple degradation of unwanted proteins in an eco-friendly method. Addition of proteases to fermentation vats has been shown to increase fermentation rates and ethanol production (See Johnston, D. and McAlbon, A. 2014 "Protease Increases Fermentation Rate and Ethanol Yield in Dry Grind Ethanol Production" *Bioresource Technology* 154:18-25).

References referred to herein are incorporated herein by reference. The following examples are provided for the purpose of exemplification and are not intended to be limiting.

EXAMPLES

Example 1

Determination of *Bacillus Subtilis* 6A-1 Identity

Biochemical and phenotypic characterization of *Bacillus subtilis* 6A-1 was performed using API 20 E identification test strips (BioMerieux 20 100) and API 50 CH 50 carbohydrate fermentation test strips (BioMerieux 50 300). The resulting biochemical profile of *Bacillus subtilis* 6A-1 was 94% similar to that of *Bacillus subtilis*.

Confirmation of this classification was performed through genomic sequencing. DNA was extracted (Fast DNA stool mini kit Qiagen) from a pure culture of *Bacillus* 6A-1 and sequenced by a contractor (GeneWiz, Inc.) on an Illumina MiSeq system using a shotgun-sequencing approach. The DNA sequences were processed by using MOTHUR (Kozich, J. J., S. L. Westcott, N. T. Baxter, S. K. Highlander, and P. D. Schloss. 2013. Development of a dual-index sequencing strategy and curation pipeline for analyzing amplicon sequence data on the MiSeq Illumina sequencing platform. *Appl Environ Microbiol.* 79(17):5112-5120). Briefly, forward and reverse reads were assembled into continuous DNA sequences ranging in length from approximately 150 to 300 base pairs. Sequences containing ambiguous base calls, long homo-polymer regions, or less than 20 bases of overlap between forward and reverse reads were eliminated from the dataset. Approximately 4.45 million sequences passed these quality control procedures and were retained as a library of shotgun DNA sequences. The consensus sequence of *Bacillus subtilis* 6A-1 is SEQ ID NO: 1. The 4.45 million sequences were aligned with the complete genome sequence of *Bacillus subtilis* strain 168. Approximately 93.1% (4.15 million sequences) belonging to the *Bacillus* 6A-1 library aligned with the reference strain with approximately 89.0% coverage. Third party verification (GeneWiz, Inc.) of genome similarity between *Bacillus* 6A-1 and *Bacillus subtilis* strain 168. The *Bacillus* 6A-1 library was mapped to the reference genome of *Bacillus subtilis* strain 168 (See GenBank Ref No. AL009126 "*Bacillus subtilis* subsp. *Subtilis* str. 168 complete genome" February 2015; NCBI RefSeq NC_000964.3 Aug. 3, 2016) by using CLC genomics workbench software (CLC Bio, Inc.) to produce a consensus partial genome sequence for *Bacillus* 6A-1. The consensus mapped sequence (internal accession number AL009126.3) was aligned with the reference sequence using BLASTn alignment software (NCBI) and was found to align with approximately 89% coverage and 98.9% sequence similarity. These results support classification of *Bacillus* 6A-1 as a subspecies of *Bacillus subtilis*.

A secondary analysis of 16S ribosomal gene similarity, widely recognized as a method of taxonomic assignment, was conducted to compare *Bacillus* 6A-1 with *Bacillus subtilis* strain 168. A subset of 29,044 DNA sequence fragments was identified in the *Bacillus* 6A-1 shotgun library that aligned with the 16S gene of *Bacillus subtilis* 168. Guided-assembly software (DNA Baser v4.31.0) was used to re-construct the 16S sequence fragments into a consensus DNA sequence. Guided assembly was iterated 10 times, and then the consensus sequences produced by each iteration were aligned by using iterative multiple sequence alignment software (MUSCLE, EMBL-EBI). The consensus 16S gene sequence produced by MUSCLE was aligned with the *Bacillus subtilis* 168 16S gene sequence by using BLASTn. The 16S ribosomal gene sequence of *Bacillus* 6A-1 was 99.8% similar (1552 out of 1554 residues). Querying the 16S ribosomal sequence against the non-redundant nucleotide database (NCBI) demonstrated greater than 99% similarity with numerous other strains of *Bacillus subtilis*. Thus, *Bacillus* 6A-1 can be classified as a subspecies of *Bacillus subtilis* on the basis of both 16S and whole-genome shotgun sequencing.

Example 2

Production of Enzyme-Containing Extract from *Bacillus subtilis* 6A-1

An 8 hour aerobic culture of *Bacillus subtilis* 6A-1 was prepared using Minimal *Bacillus* Media (MBM) (composition: Sucrose 10.0 g/L, $K_2HPO_4$ 2.5 g/L, $KH_2PO_4$ 2.5 g/L, $(NH_4)2HPO_4$ 1.0 g/L, $MgSO_47H_2O$, $FeSO_47H_2O$ 0.01 g/L, $MnSO_47H_2O$ 0.007 g/L Reference: *Bacillus* and related endospore-forming bacteria. Bioscience Portal "Biology-Life Science-Edu-Lecture Notes." Nov. 9, 2013. Table 2. https://bioscienceportal.wordpress.com/2013/11/09/bacillus-and-related-endospore-forming-bacteria/) which was amended by replacing Sucrose with Dextrose (10 g/L), and adding $CaCl_2$ (0.12 g/L), $MnCl_2$ (0.05 g/L), and 1% (w/v) Bacto Soytone (BD 243620). The bacterium was incubated at 30° C. for 8 hours. At the end of the incubation period, the bacterial cells were separated from the broth using centrifugation followed by filtration using a 0.45 micron filter. Cellulolytic activity was assayed using the method detailed below. The liquid extracts were then subjected to tests for enzyme activity. Results are detailed in FIG. 1.

Example 3

Cellulase and Amylase Enzyme Activity Determination

One unit of cellulase or amylase activity is defined as the quantity of enzyme that liberates 1 micromole of reducing sugar (expressed as glucose equivalents) per minute from the appropriate substrate under the conditions of the assay described. The cellulase substrate is sodium carboxymethyl cellulose. The amylase substrate is soluble starch (suitable for diastase measurement). For the purposes of this assay substrate and cellulase enzymes reacted in 0.015 M Sodium Acetate Buffer, pH 5.0, prepared from sodium acetate trihydrate and acetic acid. For the purposes of this assay substrate and amylase enzymes reacted in 0.02 M Sodium Phosphate Buffer, pH 6.0, prepared from sodium 0.2M dibasic sodium phosphate and 0.2M monobasic sodium phosphate, corrected to pH 6.0 using 0.1N sodium hydroxide or 0.1N hydrochloric acid.

Glucose standards were prepared in deionized water and a standard curve was constructed for a range of glucose solutions from 0.1 mg/mL to 1.0 mg/mL. To each 0.8 mL of glucose dilution in a glass tube, 1.2 mL of DNS Reagent (1.0% 3,5-dinitro-salicylic acid solution (DNS) was prepared in 0.4 N NaOH with 300 g/L of potassium sodium tartrate.) was added. The tubes containing the standard glucose solutions were placed in boiling water bath for 10 minutes, after which they were cooled rapidly in ice water bath. 2.0 mL of deionized of reducing sugar was read in suitable tubes in a spectrophotometer at 540 nm wavelength water was added to each tube. The reddish orange color developed by the DNS reagent in presence.

A 1.0% Sodium carboxycellulose (CMC) Substrate Solution was prepared from low viscosity carboxymethyl cellulose sodium salt (degree of substitution of 0.60-0.95-viscosity 3,000-6,000 cps). The substrate solution was prepared in the boiling 0.015 M Acetate Buffer which was stirred until substrate was dissolved and tempered in water bath to assay temperature.

The 1% Starch Substrate Solution was prepared by dissolving 1.0 g soluble starch was 90 ml of hot 0.02 M sodium phosphate buffer. Temperature was elevated to gently boil to dissolve substrate. pH was rechecked and adjusted to pH 6.0 with 0.1N sodium hydroxide, if necessary. Volume was adjusted to 100 ml in volumetric flask with buffer. Substrate was tempered in water bath to assay temperature.

The liquid enzyme-containing samples were analyzed in the following manner: to each tube containing 0.40 mL of 1% substrate solution was added 0.40 mL of enzyme-containing solution. After mixing, tubes were incubated at 40° C. for 30.0 minutes. After incubation, 1.2 mL of DNS was added to each tube. Tubes were subjected to a boiling water bath for 10.0 min after which they were immersed in an ice water bath and 2.0 mL of deionized water was added to each tube. The absorbance of the each aliquot of reactant mixture was read in spectrophotometer in suitable tubes at 540 nm wavelength. Each of the samples was run in triplicate for greater accuracy.

One unit of cellulase or amylase activity (DNS method) is defined as the quantity of enzyme that liberates 1.0 micromole of reducing sugar (expressed as glucose equivalents) per minute under the standard conditions of the assay described.

The absorbance value for each enzyme-containing sample was calculated by subtracting the enzyme blank value from the enzyme sample value. The net value was used to calculate the activity value from the standard glucose curve.

$$\text{Activity(Enzyme activity/gram)} = \frac{[\text{Activity value from standard curve} \times \text{dilution}]}{[\text{Micromoles glucose} \times \text{reaction time}]}$$

See FIG. 1.

Example 4

Figure 2:
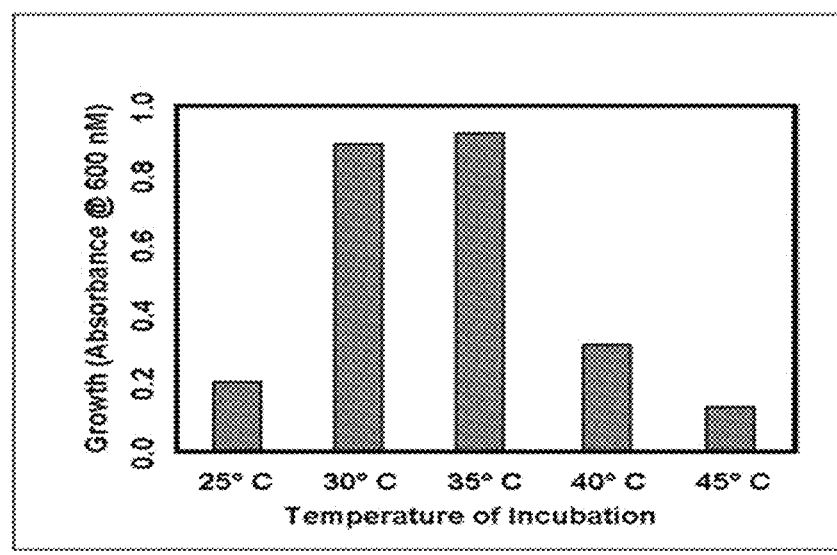
FIG. 2 is a graph showing *Bacillus subtilis* 6A-1 growth relative to temperature.

Growth of *Bacillus subtilis* 6A-1 vs Temperature 100 mL aliquots of Brain Heart Infusion broth were inoculated with 1 mL each of broth containing viable *Bacillus subtilis* 6A-1 cells. After inoculation individual aliquots were incubated at the different temperatures indicated for 12 hours with agitation. Absorbance (optical density) readings (which are direct indicators of bacterial growth and multiplication) were taken at a wavelength of 600 nm. It is apparent from the data presented in FIG. 2 that the optimal temperature for *Bacillus subtilis* 6A-1 growth is 30°-35° Celsius. Growth rates and levels declined steeply at temperatures outside this temperature range. This data indicates that *Bacillus subtilis* 6A-1 is a mesophilic bacterium.

Example 5

Figure 3:
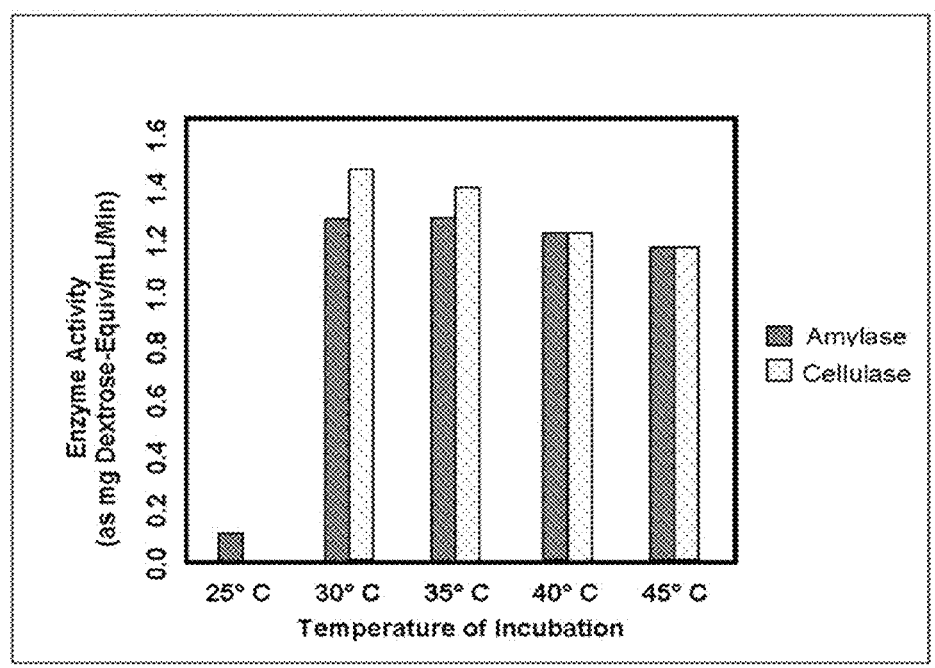
FIG. 3 is a graph showing *Bacillus subtilis* 6A-1 enzyme production relative to temperature. The gray bar shows amylase production and the dotted bar shows cellulose production.

*Bacillus subtilis* 6A-1 Enzyme Production at Different TemperaturesAliquots of 100 mL of Brain Heart Infusion broth were inoculated with 1.0 mL of broth containing viable *Bacillus subtilis* 6A-1 cells. The inoculated broth was incubated at the temperatures indicated for 12 hours with agitation. Samples of broth were taken at the 12 hour point and each sample was centrifuged at 3000 rpm for 20 min. The supernatant was harvested. These broth supernatant samples were analyzed for cellulase and amylase activity using the CMC-DNS and Starch-DNS Method described above. Results are reported in FIG. 3. The experiment indicated that the optimal temperature range for amylase and cellulase production by *Bacillus subtilis* 6A-1 is in the 30°-35° Celsius range. Cellulase and amylase activity was assessed using the protocol described in Cellulase and Amylase Enzyme Activity Determination.

Example 6

Enzyme Activity on Polysaccharides

Growth experiments and detailed examinations of this bacterium revealed that the strain excreted enzymes which exhibit novel cellulase activity over a broad pH range.

Figure 4:
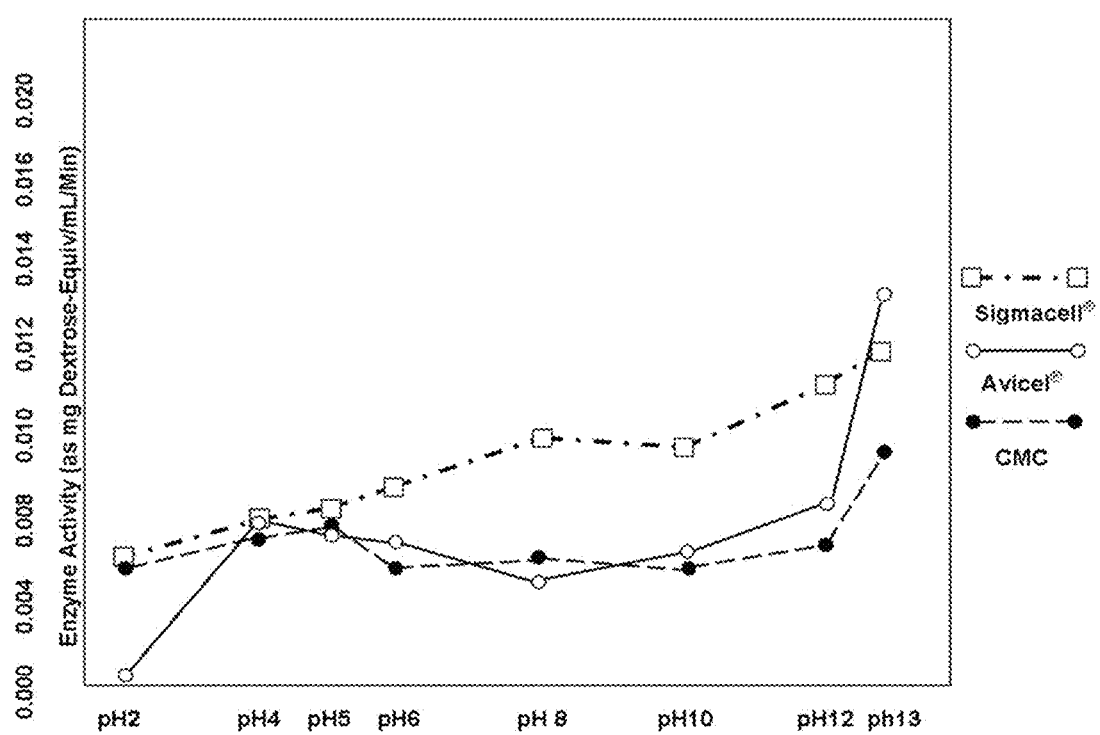
FIG. 4 is a graph showing *Bacillus subtilis* 6A-1 enzyme activity on three types of cellulose at various pH levels. The dash and dot line shows activity the microcrystalline cellulose Sigmacell® cellulose, the straight line shows activity on the Avicel® cellulose.

The bacteria produced hydrolytic enzymes. It was discovered by the inventors that the *Bacillus subtilis* 6A-1 (SD-6861) produced three protein fractions and exhibited activity not only on carboxymethyl cellulose (CMC), a compound that is the result of chemically modifying cellulose to render it more soluble, but also on native, crystalline cellulose. Examples of commercial versions of purified, crystalline, water-insoluble cellulose are SigmaCell® and Avicel®. Avicel® used for this research was Avicel® (Type PH 101) (CAS 9004-34-6) manufactured and supplied by FMC Biopolymer (FMC BioPolymer 1735 Market Street Philadelphia, Pa. 19103). Sigmacell® (Catalog Number S3504) is marketed by Sigma-Aldrich® and is a microcrystalline cellulose preparation of finely divided microcrystalline cellulose which retains crystalline integrity but can be more easily dispersed in aqueous suspensions. The protein fractions showed this activity over a broad pH range from pH 2.0-13 (See FIG. 4).

Aliquots of 1 mL of enzyme-containing broth were added to aliquots of 4 mL of the appropriate pH buffer (See Buffer Solutions—below) along with 0.10 g of polysaccharide to be tested. The reactant mixtures were incubated with agitation at 40° C. At the end of incubation time (1 hour), the reacting mixture was chilled in a 0° C. ice bath and filtered through a 0.45 micron filter. 450 µL of each sample was withdrawn and analyzed for reducing sugar generated by the enzyme reacting with the said polysaccharide by the method of Miloski et. al. (2008)—Miloski, K., Wallace, K., Fenger, A., Schneider, E., and Bendinskas, K. "Comparison of Biochemical and Chemical Digestion and Detection Methods for Carbohydrates." *American Journal of Undergraduate Research*. 2008. 7 (2):7-18.

The 450 µL aliquot of each sample was pipetted into new microfuge tubes. A 450 µL aliquot of 3,5-dinitrosalicylic acid (1%) prepared in 0.4N NaOH was added to each tube. Samples were immersed in a 90° C. hot water bath for 10 minutes. After removal from the bath, 150 µL of sodium potassium tartrate (40%) was added to each tube. A 300 µL aliquot of each sample was pipetted into separate wells of a 96-well microplate. Absorbance was read at 575 nanometers with a plate reader and the average absorbance for each triplicate set was calculated.

| Buffer Solutions | |
|---|---|
| pH 2 | Citric Acid-$Na_2$ $HPO_4$ Preparation: Mixed 89.1 mL of 0.1M Citric Acid and 10.90 mL of 0.2M $Na_2$ $HPO_4$ then solution titrated with 1M HCl to pH 2.0 |
| pH 4 | Citric Acid-$Na_2$ $HPO_4$ Preparation: Mixed 61.45 mL of 0.1M Citric Acid and 38.55 mL of 0.2M $Na_2$ $HPO_4$ then solution titrated with 1M HCl to pH 4.0 |
| pH 6 | Citric Acid-$Na_2$ $HPO_4$ Preparation: Mixed 36.85 mL of 0.1M Citric Acid and 63.15 mL 0.2M $Na_2$ $HPO_4$ then solution titrated with 1M HCl to pH 6.0 |
| pH 8 | $Na_2$ $HPO_4$—$NaH_2PO_4$ Preparation: Mixed 47.35 mL of 0.2M $NaH_2PO_4$ and 2.65 mL of 0.2M $Na_2$ $HPO_4$ then solution titrated with 1M HCl to pH 8.0 |
| pH 10 | $Na_2CO_3$—$NaHCO_3$ Preparation: Mixed 60 mL of 0.1M $Na_2CO_3$ and 40 mL 0.1M $NaHCO_3$ then solution titrated to pH 10.0 |
| pH 12 | KCl—NaOH Preparation: Mixed 25 mL of 0.2M KCl and 6.0 of 0.2M NaOH then diluted with water to a volume of 100 mL. Rechecked pH. |
| pH 13 | KCl—NaOH Preparation: Mixed 25 mL of 0.2M KCl and 66 mL of 0.2M NaOH then diluted with water to a volume of 100 mL. Rechecked pH. |

Experimentation has shown that overall cellulolytic enzyme activity that is exhibited by *Bacillus subtilis* 6A-1 is effective upon several forms of cellulose substrate. With the commercial micro-crystalline cellulose, Avicel®, at least two peaks of cellulase activity occur, one indicating an acidophilic/neutral-acting cellulase enzyme system, another peak indicating an alkaliphilic cellulose-digesting enzyme system (See FIG. 4). At the same time, additional research has shown that the action pattern of the cellulolytic enzyme systems on carboxymethyl cellulose (CMC) is very similar. However, tests utilizing another commercial microcrystalline cellulase, Sigmacell® as substrate reveal that activity by 6A-1 cellulases are similarly active in the acidic pH ranges, and increasingly active in neutral and alkaline pH ranges. The result of this data indicates that the cellulolytic activity of the enzymes expressed and secreted by *Bacillus subtilis* 6A-1 are novel in that they are active throughout the range from pH 2.0 to pH 13.0 on chemically modified and unmodified cellulosic compounds.

The *Bacillus subtilis* 6A-1 (SD6861) produces crystalline cellulose-digesting enzymes. These enzymes are usually characterized as being exo-acting cellulases beginning their hydrolytic at the outside edges of the polymeric cellulose structure. In addition, the enzyme systems can digest modified cellulose (such as carboxymethyl cellulose or CMC). CMC-digesting enzymes are usually described as being more endo-acting cellulases, beginning their hydrolysis in the center of the polymeric cellulose structure.

The use of the strain provides optimal efficacy in a broad range of applications that a combination of cellulase activity is utilized. If one applies cellulases of different types with activity ranging over broad expanses of pH, then the greatest efficacy can often be achieved.

Biochemical processes which vary in pH throughout their progression will benefit from broad pH range efficacy. One example is an ensilage fermentation which starts at pH 6.8-7.0 and finishes at 3.5-3.9. Another example is a feeding process that involves the animal gut which may start at pH 6.6-7.0, continues through pH levels reaching 2.0 or even lower, and finishes at 6.4-6.8.

Example 7

Cellulolytic Activity on Native Sources of Polysaccharides

Figure 5:
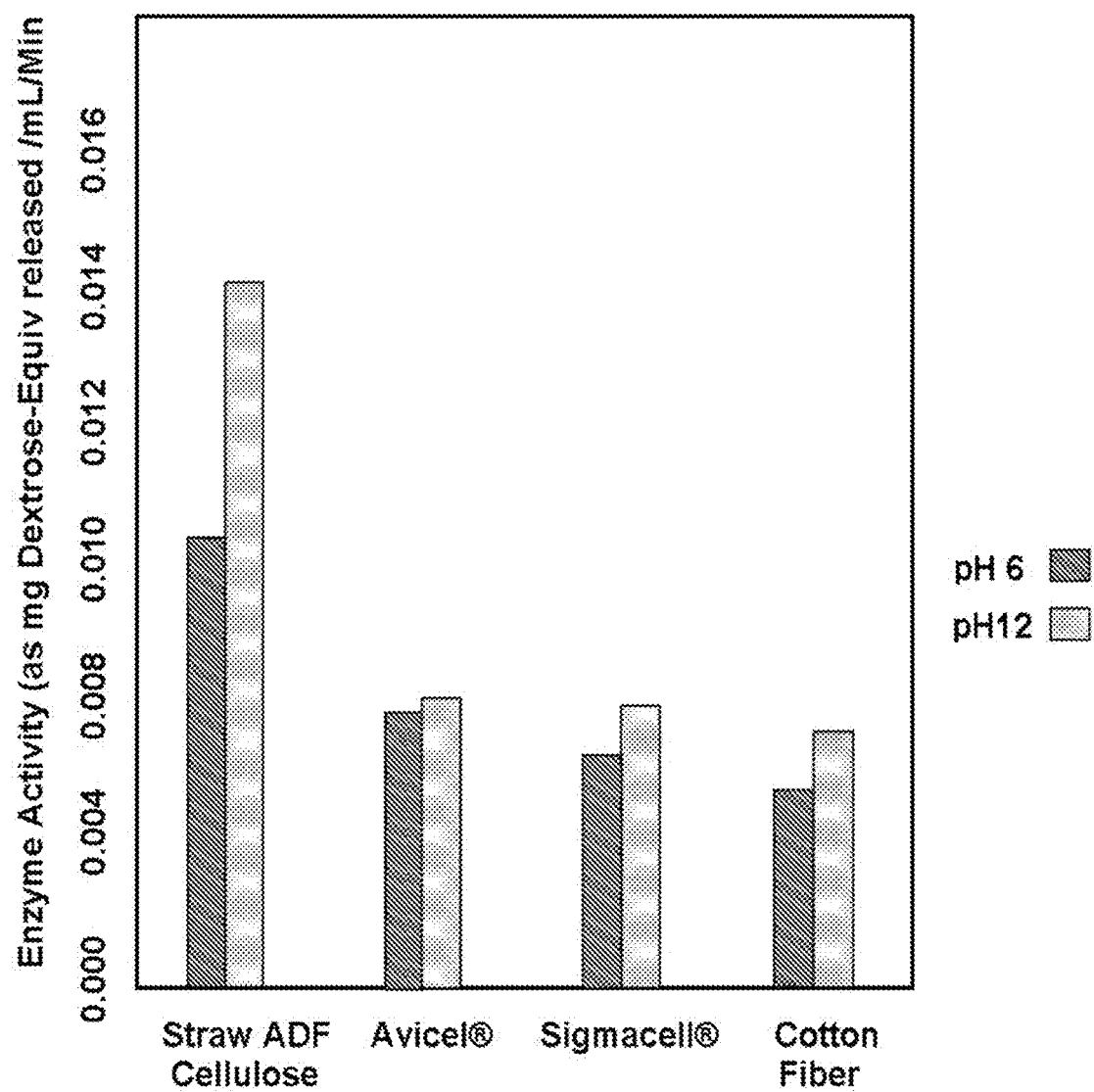
FIG. 5 is a graph showing enzyme activity on straw ADF cellulose, Avicel® cellulose, Sigmacell® cellulose and cotton fiber. The dark hatched bar shows activity at pH6, the lighter dotted bar shows activity at pH12.

Although it is definitively shown that the enzyme systems of Bacillus subtilis 6A-1 are active on several types of crystalline and modified cellulase preparations, enzyme-containing broth of Bacillus subtilis 6A-1 was additionally analyzed for its cellulolytic activity upon unmodified cellulose from native sources: delignified "ADF cellulose" derived from delignified, acid detergent fiber treatment of wheat straw, and from absorbent cotton. The results are shown in FIG. 5 below.

Native cellulose derived from delignified ADF residue: Acid Detergent Fiber was prepared from wheat straw and delignified according the following method.

A 5.0 gram sample of ground dry wheat straw (at 0.8 mm grind size) was subjected to boiling with 500 ml Acid Detergent Fiber Solution (prepared by adding 20 g cetyl trimethylammonium bromide (CTAB) to 1 L 1.00N $H_2SO_4$) for 60 minutes. The spent liquid, after 60 minutes, contained Acid Detergent Solubles which were separated by filtration. The insoluble residue was rinsed twice with hot distilled water, and subjected again to boiling with ADF solution for another 60 minutes. The final residue of the procedure was identified as ADF straw residue.

This residue, containing cellulose, lignin, and an insignificant amount of heat damaged protein and a portion of cell wall protein and minerals (ash) was subjected to saturated potassium permanganate combined with lignin buffer Solution at ratio 2:1 (see material preparation below).

The lignin buffer solution contained 6.0 g of ferric nitrate nonahydrate and 0.15 g silver nitrate made into 100 ml with distilled water. The mixture was combined with 500 ml glacial acetic acid and 5.0 g potassium acetate. The whole contents were brought to 1.0 liter by adding 400 mL of tert-butanol (2-methyl-2-propanol). 50.0 g $KMNO_4$ was dissolved in distilled water and brought to total volume of one liter with distilled water to prepare a 5% solution.

ADF straw residue was placed in a 500 ml beaker and the contents were covered with potassium permanganate solution treatment and stirred with a glass rod to a smooth paste. Refilling with potassium permanganate solution and stirring occasionally until the contents were poured into Gooche crucibles and the liquid was filtered off with aspirators as the acid drained away.

After 90 minutes the oxidizing solution was filtered to remove as much acid as possible with vacuum and the contents were treated with the demineralizing solution (50.0 g of oxalic acid dihydrate into 700 ml of 95% ethyl alcohol, then add and mix 50 ml concentrated (12N) hydrochloric and 250 ml distilled water). The treatment was repeated twice, and the cellulosic residue became white. The delignified white residue was washed with hot water until free from acid. The white residue (native wheat straw cellulose or Straw ADF Cellulose) was dried at 65° C.

Absorbent cotton (Swisspers® brand Cotton Balls Jumbo Plus—manufactured by U.S. Cotton, LLC, 15501 Industrial Parkway, Cleveland, Ohio 44135) was obtained commercially for use in the analytical procedure. For the analytical procedure, approximately 0.1 g was cut and placed in tubes used for the enzyme hydrolysis.

Both the straw ADF cellulose and the cotton substrates were tested for susceptibility to Bacillus subtilis 6A-1 cellulase enzymes by applying enzyme-containing broth and the enzyme activity was calculated in the same manner as in previously described experiments (Enzyme Activity on Polysaccharides). For contemporaneous comparison, the analysis set also included Avicel® and Sigmacell®1 substrates as in previous experiments. FIG. 5 illustrates the results of the test. The results again confirm the broad activity on Avicel® and Sigmacell® microcrystalline celluloses, but also reveal that the enzymes of 6A-1 also act upon native straw cellulose, and native cotton cellulose over broad range of pH values.

Figure 6:
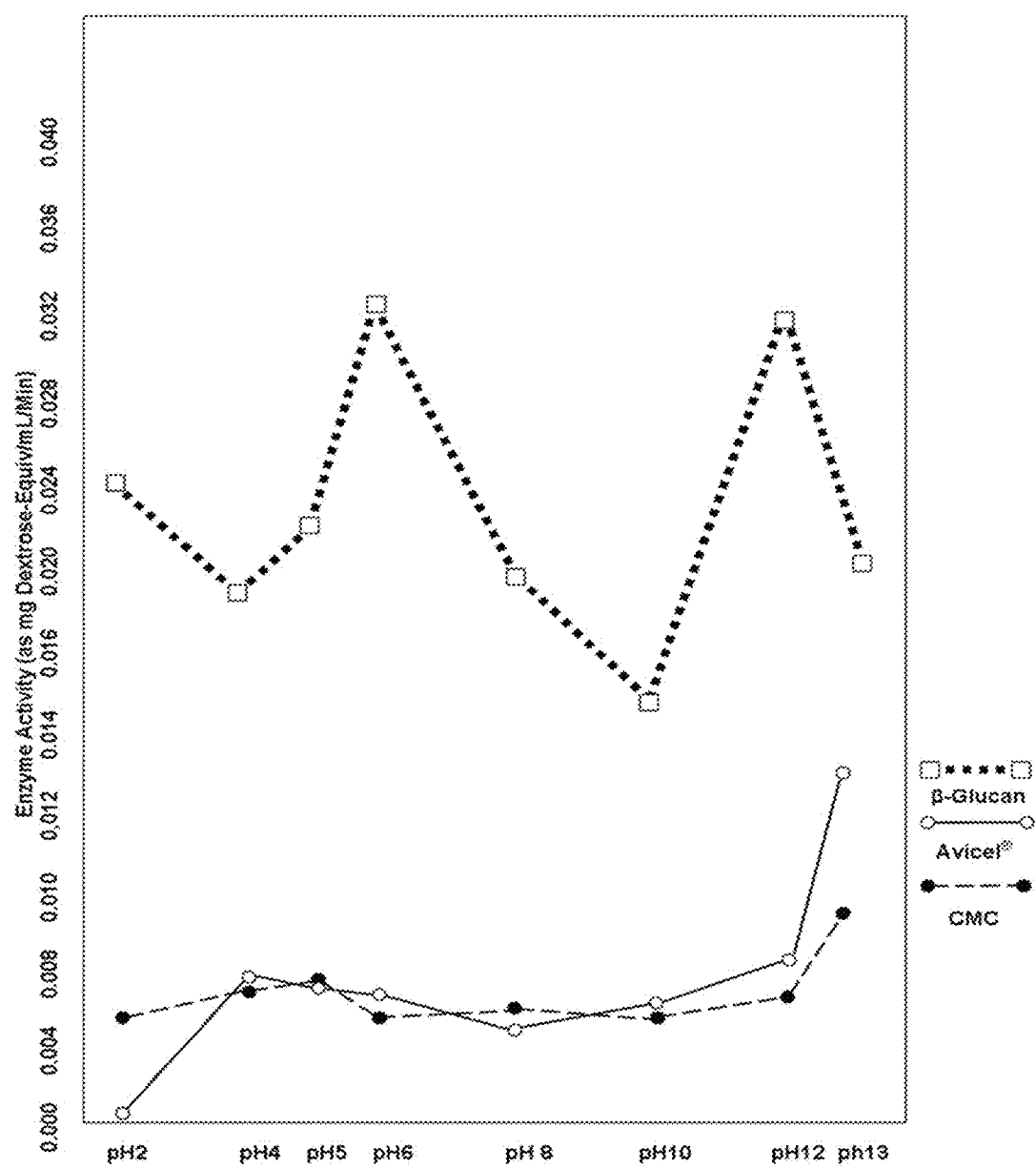
FIG. 6 is a graph showing *Bacillus subtilis* 6A-1 enzyme activity on β-glucan (from barley) at various pH levels as compared to activity on Avicel® and carboxymethyl cellulose.

FIG. 6 summarizes Bacillus subtilis 6A-1 β-glucanase activity on barley β-glucan along with comparative cellulase activity on two types of cellulose provided for reference. Cellulose and the β-glucan from certain grains and legumes represent separate types of β-glucan compounds with similar linkage. Native cellulose and micro-crystalline cellulose are β-glucans, but their structure is more crystalline in nature and less vulnerable to hydrolytic attack by bacterial enzymes. Nevertheless, it is apparent that enzymes produced and secreted by 6A-1 are capable of degrading both cellulose and barley β-glucans.

While the β-glucanase activity of enzymes produced by Bacillus subtilis 6A-1 are effective on barley β-glucan over the broad pH range of 2.0-13.0, there are peaks of activity at approximately pH 2.0, 5.0, and 12.0. These activity peaks almost assuredly point to more than one enzyme being present which can catalyze the hydrolysis of barley β-glucan. Barley β-glucan is but one example of this type of NSP present in oats, soy beans and their derivatives and other more difficult-to-digest grains and legumes. β-glucans represent one class of compound that is present in animal feedstuffs that is difficult to digest by certain livestock and poultry.

Further, Bacillus subtilis 6A-1 is unique in that the bacterium produces other enzymes which catalyze the hydrolysis of polysaccharides other than barley β-glucan and cellulose. We have discovered that the bacterium is also capable of producing enzymes which degrade the following compounds:

Lichenin (CAS 1402-10-4)—A complex β-glucan which can be isolated from Icelandic moss. According to several references, lichenin (also known as lichenan) consists of a polysaccharide with repeating glucose units linked by β-1,3 and β-1,4 glycosidic bonds.
(Perlin, A. S. and S. Suzuki. The Structure of lichenin: Selective Enzymolysis. *Canadian Journal of Chemistry*. Volume 40 (1962))

Laminarin—which is an NSP made up of β (1→3) (linked) glucan structure with β (1→6) (linked) branch points. It is a linear polysaccharide. Its hydrolysis is catalyzed by enzymes such as laminarinase (EC 3.2.1.6) that breaks the β (1→3) bonds. (Salyers A A, Palmer J K, Wilkins T D. Laminarinase (beta-glucanase) activity in *Bacteroides* from the human colon. *Appl Environ Microbiol*. (May 1977). (England) 33 (5): 1118-1124))

Xylan (CAS 9014-63-5)—which is composed of hemicelluloses that are found in plant cell walls and in some algae. Xylans are polysaccharides constructed from units of xylose. Xylans are almost as ubiquitous as cellulose in plant cell walls and contain predominantly β-D-xylose units linked in similar manner to the monomers in cellulose. (Alonso J L, Dominguez H, Garrote G, Parajo J C, Vazques M J (2003). "Xylooligosaccharides: properties and production technologies". *Electron. J. Environ. Agric. Food Chem*

2 (1): 230-232; M. L. T. M. Polizeli, A. C. S. Rizzatti, R. Monti, H. F. Terenzi, J. A. Jorge, D. S. Amorim. Xylanases from fungi: properties and industrial applications. Appl Microbiol Biotechnol (2005) 67: 577-591; K. Beg •M. Kapoor •L. Mahajan •G. S. Hoondal, Microbial xylanases and their industrial applications: a review Appl Microbiol Biotechnol (2001).)

Starch (CAS 9005-25-8)—an α-glucan, which is the predominant carbohydrate storage compound of potatoes, corn and other vegetables and grain. Unlike the polysaccharides above, starch is composed of amylose (CAS 9005-82-7) and amylopectin (CAS 9037-22-3) which are polymers of predominantly α (1→4) linked glucose monomers. Amylose is a straight chained polymer with α (1→4) linked monomers, while amylopectin is branching polymer linked predominantly by α (1→4) linked glucose monomers, but with α (1→6) branch points.

Figure 7:
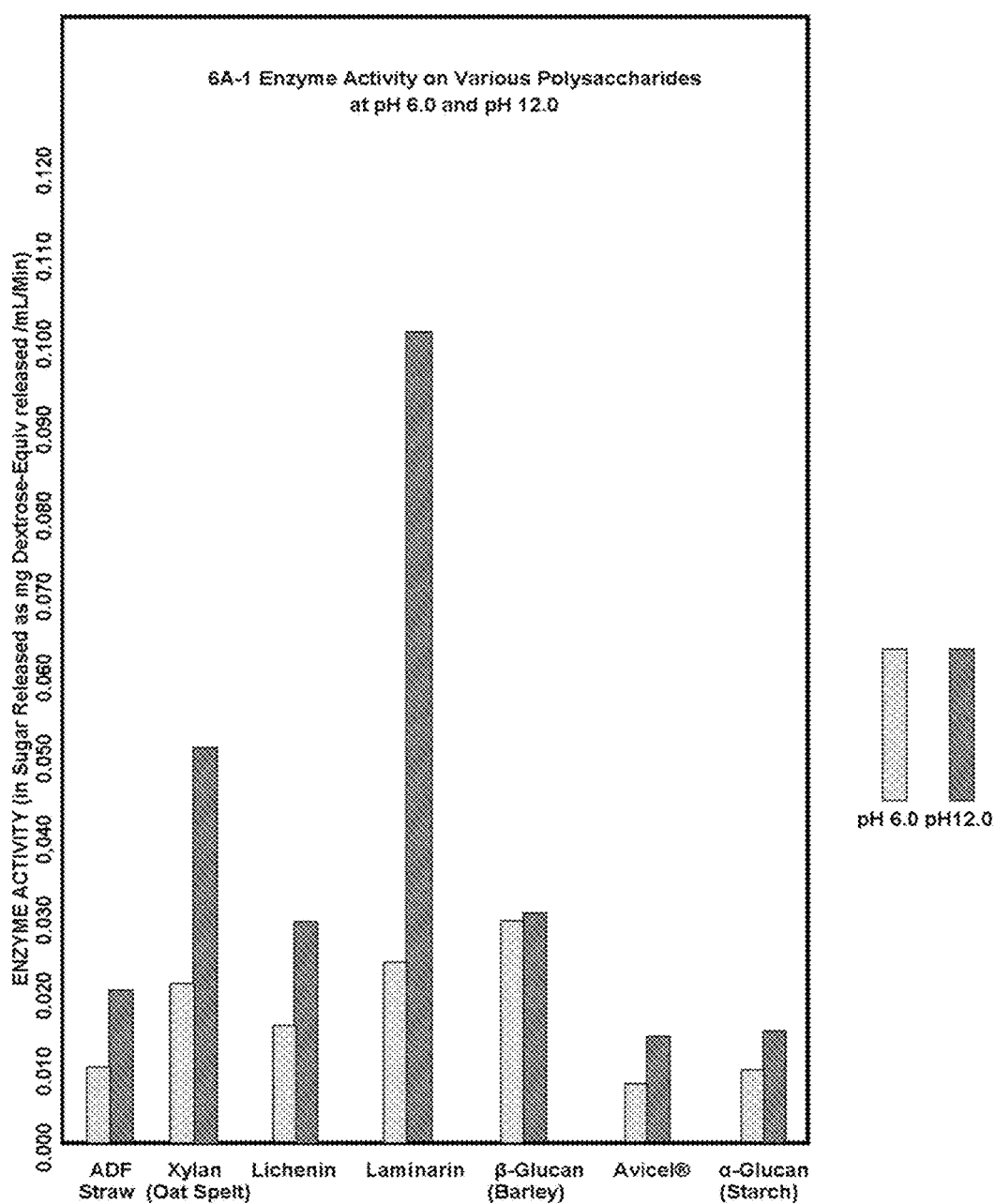
FIG. 7 is a graph showing *Bacillus subtilis* 6A-1 enzyme activity on various polysaccharides at pH6.0 and pH 12.0. The light gray bar shows activity and pH 6.0 and the dark gray bar show activity at pH 12.0.
Figure 8:
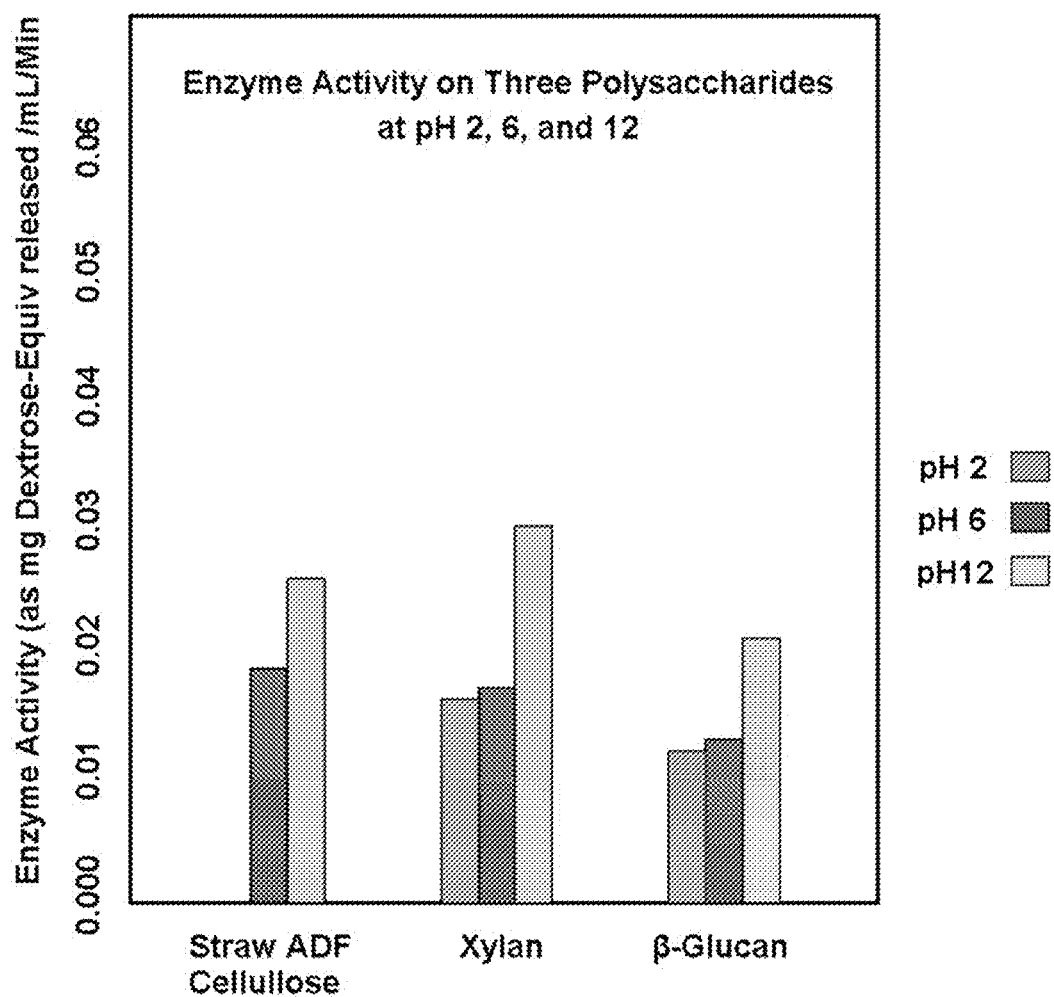
FIG. 8 shows *Bacillus subtilis* 6A-1 activity on three polysaccharides at pH 2.0, 6.0 and 12.0. The gray bar with hatched lines to the right shows activity at pH 2.0, the dark gray bar with hatched lines to the left shows activity at pH 6.0 and the dotted bar shows activity at pH 12.0.

The enzymes which catalyze the hydrolysis of starch are known as (EC 3.2.1). The predominant amylase produced by bacilli is alpha-amylase (EC 3.2.1.1) (CAS 9014-71-5). FIGS. 7 and 8 illustrate the hydrolytic catalyzing activity of the enzymes produced by *Bacillus subtilis* 6A-1 on these diverse polymeric carbohydrate compounds: starch and non-starch polysaccharides. The enzymes expressed and excreted by *Bacillus subtilis* 6A-1 exhibit activity in the neutral area (pH 6.0) and in the highly alkaline area (pH 12.0) of the pH scale. The protocol for the experiment employed the procedures described above at Enzyme Activity on Polysaccharides.

*Bacillus subtilis* 6A-1 strain cells, spores, and enzymes produced can reduce flatulence compared to a feed which does not comprise 6A-1, cells or spores or enzymes. Flatulence in animals may occur due to bacterial action upon undigested and unassimilated nonstarch polysaccharides. This flatulence includes production of gases during digestion such as methane ($CH_4$) and other greenhouse gases that present an environmental or safety issue with certain livestock and other animals.

Example 8

Activity of *Bacillus subtilis* 6A-1 on Acid Detergent Fiber Residue

Acid Detergent Fiber (ADF) residue is the fraction of feed which is a component produced during routine feed analysis. ADF represents the fiber portion of the feed sample that is most difficult for animals to digest. A sample of straw fiber was subjected to standard procedures for production and measurement of ADF (See procedure in Cellulolytic Activity on Native Sources of Polysaccharides). The ADF portion which contained 17% lignin was subjected to attack by 100 microliters of enzyme-containing fermentation broth supernatant from *Bacillus subtilis* 6A-1. A sample of ADF residue so treated would be composed of cellulose and lignin.

Figure 9:
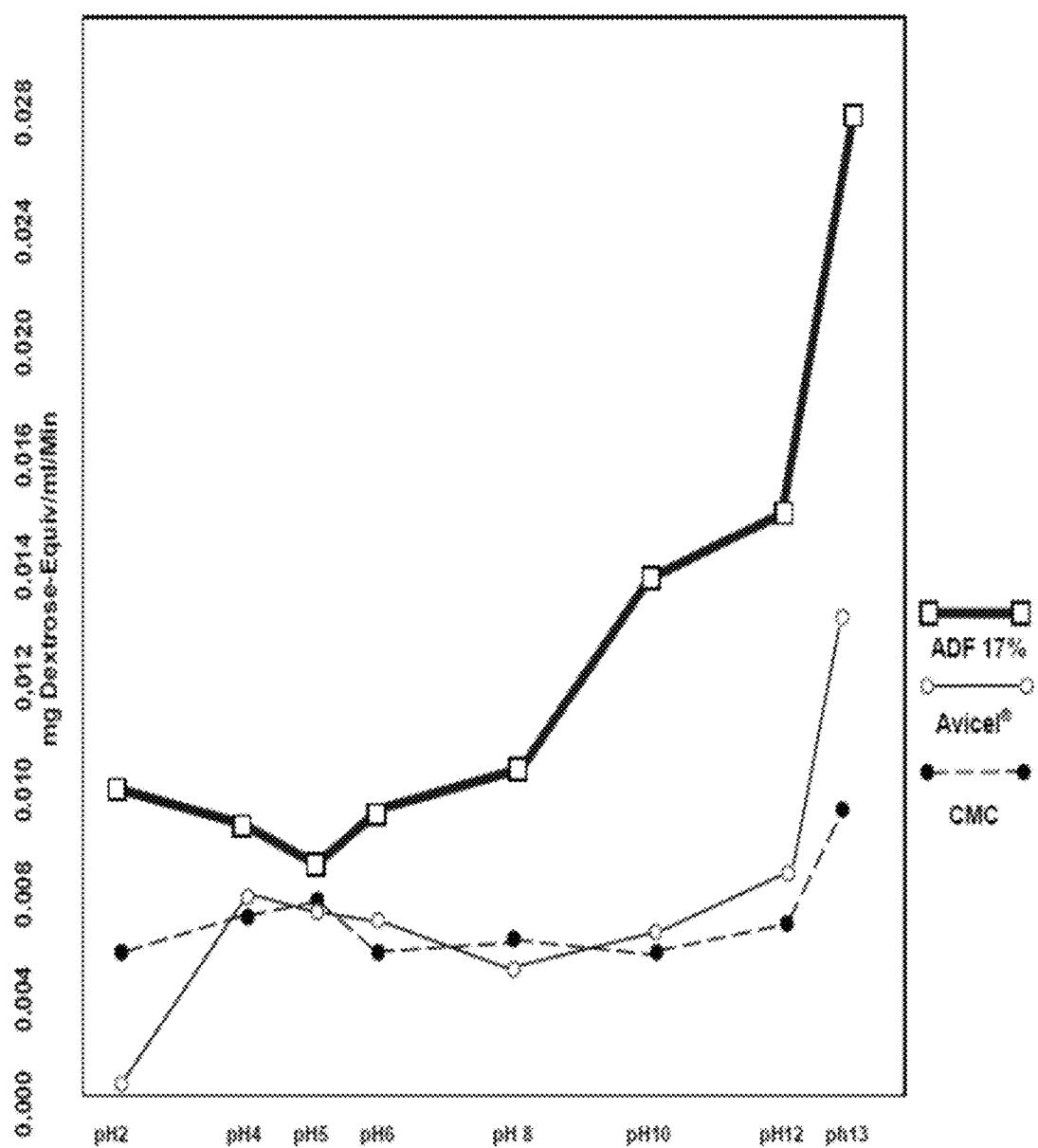
FIG. 9 shows sugar released from Avicel® celluloses and carboxymethyl cellulose (CMC) and Acid Detergent Fiber (ADF) 17% lignin (from straw) at various pH levels upon contact with *Bacillus subtilis* 6A-1 broth (100 μl). The line with square points is ADF 17%, the open circles are Avicel® and the darkened circles are CMC.
Figure 10:
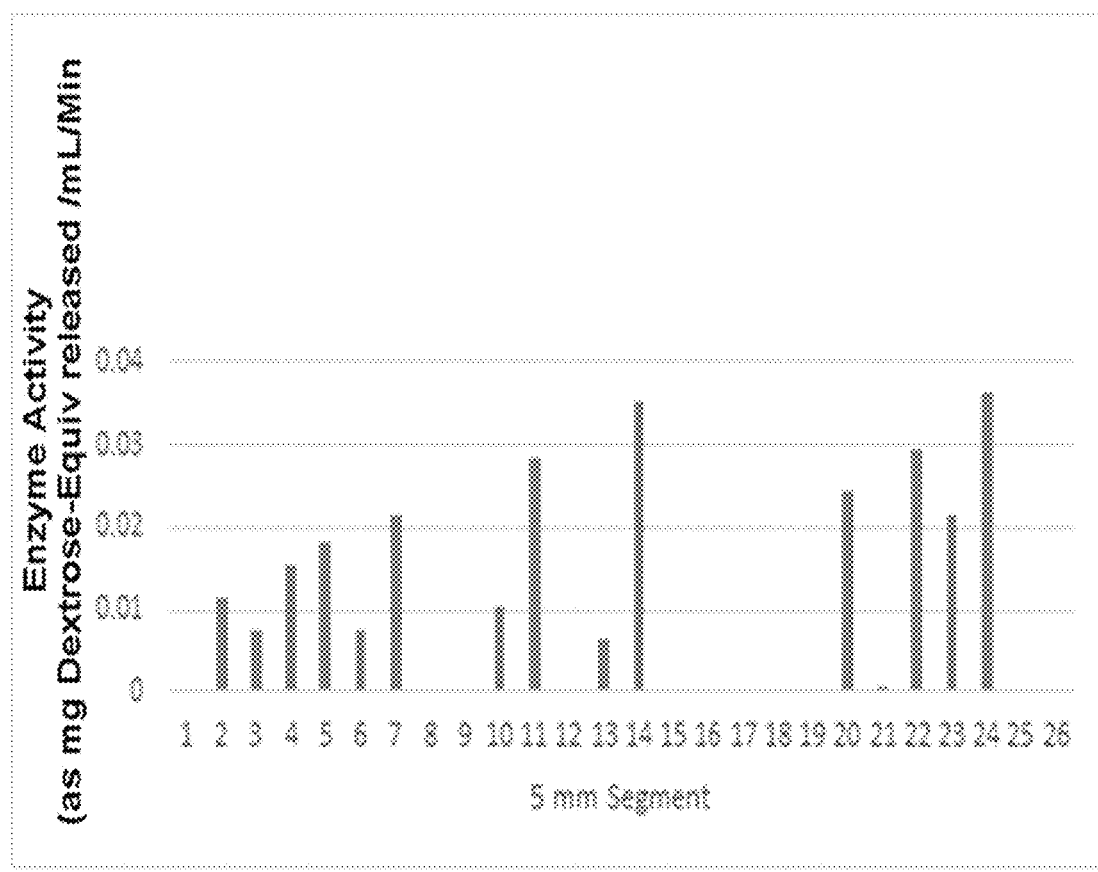
FIG. 10 is a graph showing *Bacillus subtilis* 6A-1 cellulase activity measured by Cellulase and Amylase Enzyme Activity Determination at a pH of 6.3.
Figure 11:
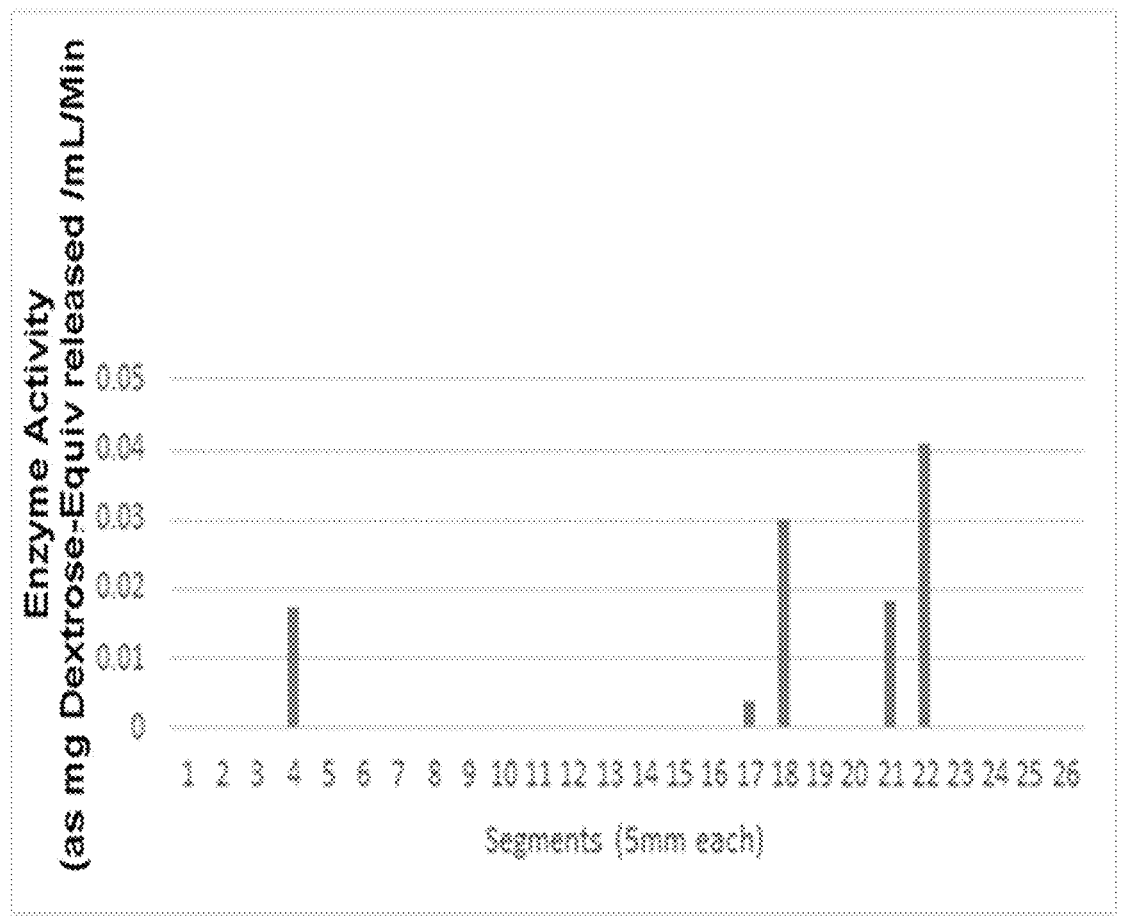
FIG. 11 is a graph showing cellulose activity measure by Cellulase and Amylase Enzyme Activity Determination at pH of 11.12.
Figure 12:
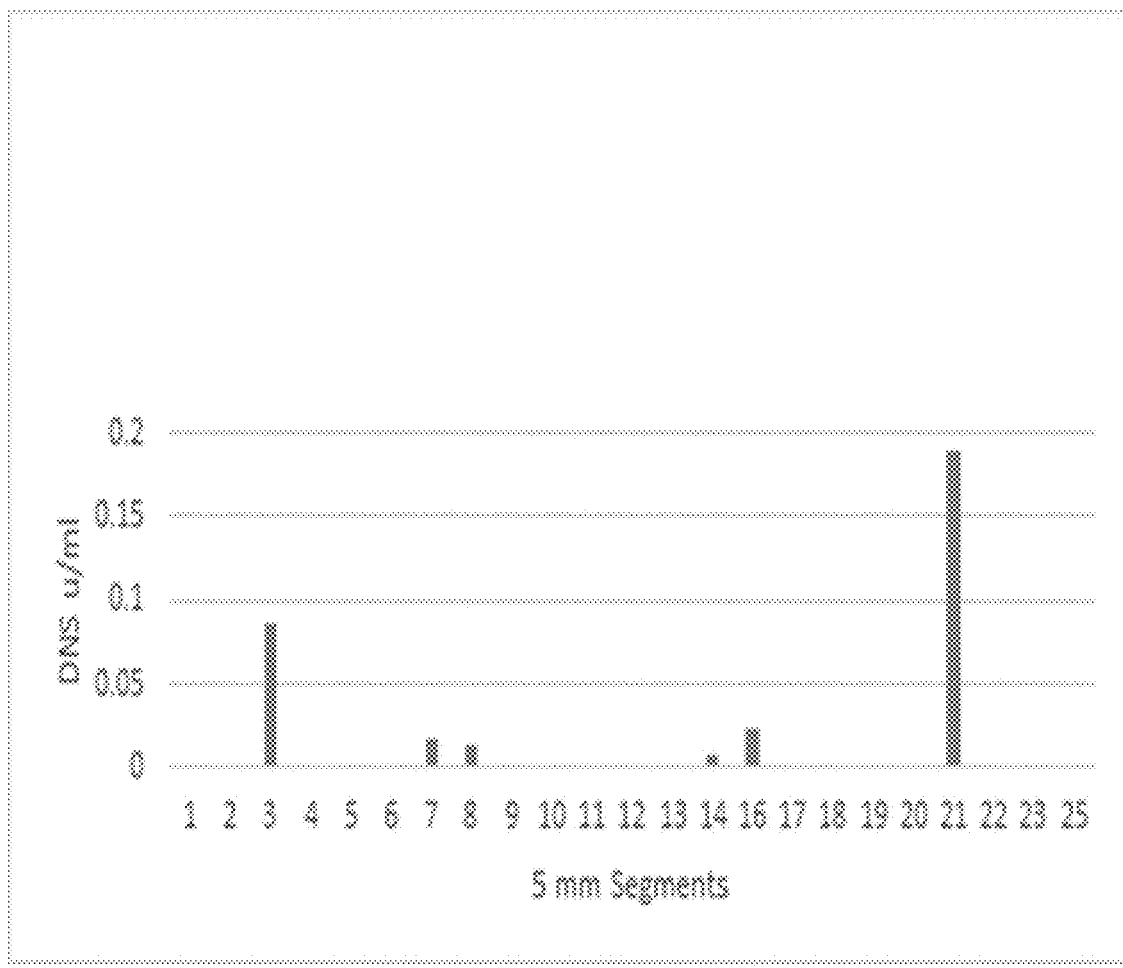
FIG. 12 is a graph showing digestion of Avicel® cellulose using β-alanine acetic acid 8% PAG gel segment elutions at a pH of 6.3.
Figure 13:
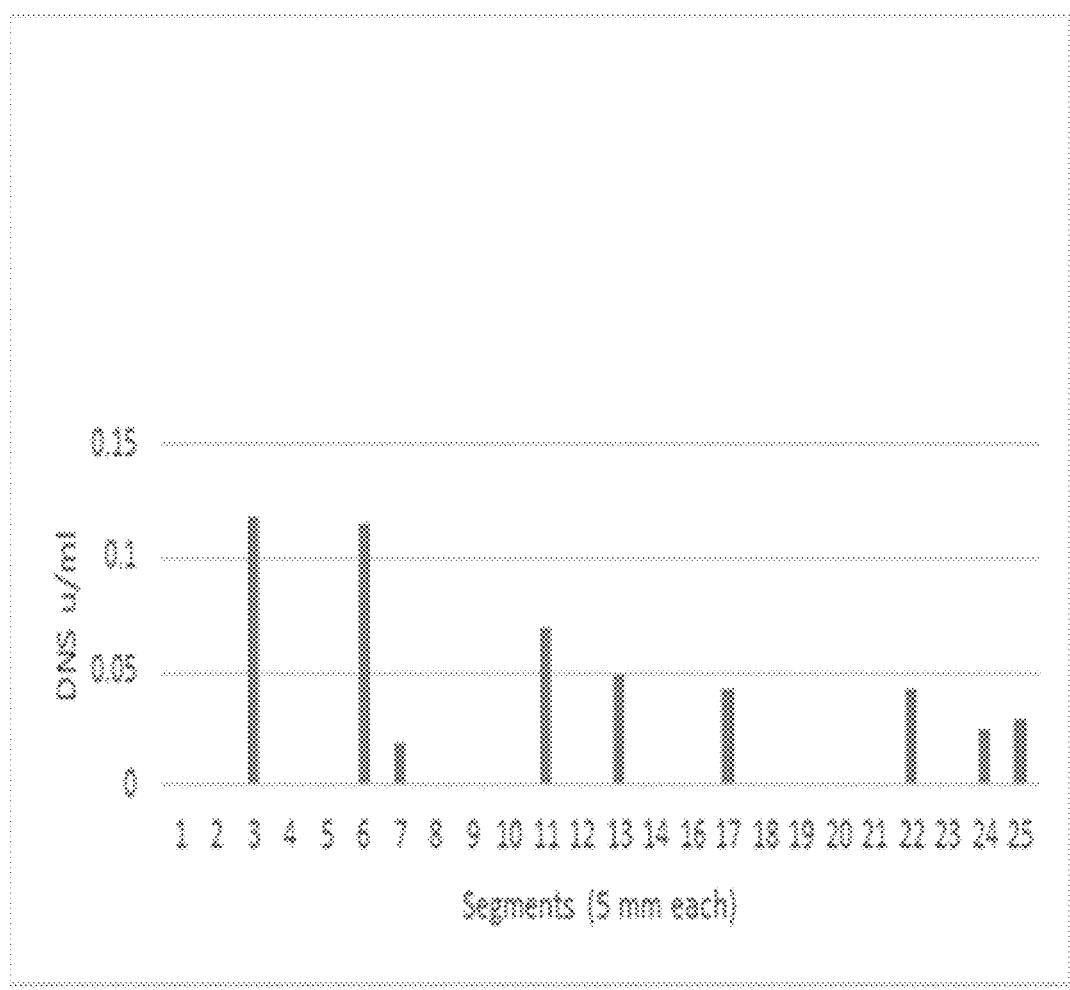
FIG. 13 is a graph showing digestion of Avicel® cellulose using β-alanine acetic acid 8% PAG gel segment elutions at a pH of 11.12.

FIG. 9 graphically represents the activity of the enzymes from *Bacillus subtilis* 6A-1 on native cellulose extracted chemically from wheat straw. The data reveals that hydrolytic digestion of the cellulose in the ADF fraction occurs from pH 2 to pH 13, with the highest levels of sugar-producing hydrolytic activity occurring at the lowest range of pH (2.0) and at the highest point of monitoring (pH 13.0). The experiment below used the protocol described above in Enzyme Activity on Polysaccharides.

ADF residue fractions of feedstuffs can be in the range of 3% to 95%. ADF may be, for example, about 3% in corn and 95% in small grain straw residue. Small grains include, for example: wheat, barley, triticale, rye, oats, and spelt. Small grain straws may also include rice straw and stems or non-grain components of certain other crops indigenous to other specific geographic areas such as rice straw and hulls, and maize and sorghum stover.

Example 9

Separation and Characterization of Cellulolytic Enzyme Fractions from *Bacillus subtilis* 6A-1

Subsequent separation of active cellulolytic enzyme proteins via electrophoresis, according to the method of de Lourdes et al. (Maria de Lourdes T. M. Polizeli, Simone C. Peixoto-Nogueria, Tony M. da Silva, Alexandre Mailer and Hamilton Cabral (2012). Gel Electrophoresis for Investigation Enzymes with Biotechnological Application, Gel Electrophoresis—Advanced Techniquies, Dr. Samah Magdeldin (Ed.), ISBM: 978-953-51-0457-5, In Tech, Available from worldwide webintechopen.com/books/gel-electrophoresis-advanced-techniques/enzymes-with-biotechnological-application), have revealed that *Bacillus subtilis* 6A-1 produces three distinct and separate enzyme fractions which demonstrate hydrolytic enzyme activity toward fiber, using CMC and microcrystalline cellulose (Avicel®) as a substrate. (See FIGS. 10, 11, 12 and 13)

The CMC-DNS assay is described above (Cellulase and Amylase Enzyme Activity Determination). See below for the variation of the analysis which requires elution of the active cellulase enzymes which may be imbedded in the polyacrylamide gel slices prior to running the DNS cellulase procedure described above.

Cellulase enzyme fractions which were produced by *Bacillus subtilis* 6A-1 were separated by polyacrylamide gel electrophoresis according to the technique described by de Lourdes, et. al. Approximately 3 mL of enzyme-containing *Bacillus subtilis* 6A-1 broth supernatant (prepared as in above Production of enzyme-containing extract from *Bacillus subtilis* 6A-1) was dialyzed 18 hours against polyethyleneglycol (PEG) 6000 solution at 4° C. The PEG solution was prepared by adding 200.0 g of PEG in 250 mL of deionized water and heating until PEG dissolved in water. The volume was adjusted to 500 mL. 200 µL of distilled water was added back to the dialyzed sample and the inside of the dialysis tubing was rinsed to obtain as much of the dialyzed enzyme-containing *Bacillus subtilis* 6A-1 broth sample as possible. An 8.0% native polyacrylamide gel electrophoresis (PAGE) gel was prepared for alkaline proteins (as specified in de Lourdes, et. al., p 102). Three wells of the gel were loaded with dialyzed *Bacillus subtilis* 6A-1 enzyme-containing supernatant and were subjected to electrophoresis at 120 V for 4.0 hours using a β-alanine acetic acid mixture as running buffer. The β-alanine acetic acid mixture consisted of 31.2 g of β-alanine, 8 mL of glacial acetic acid and an amount of distilled water sufficient to bring final volume to 1.0 L After the period of electrophoresis, the gel was sliced into 5 mm segments and each segment was placed in separate tubes containing 1 mL of 0.1 M potassium phosphate buffer at pH 7.0. The proteins were allowed to elute into the buffer solution for 48 hours at 4° C. These solutions were then assayed using a CMC-DNS assay for cellulase activity (see Cellulase and Amylase Enzyme Activity Determination). Treatments of gel samples to elute enzymes prior to analysis for CMC cellulolytic activity were the same as the method described for Avicel® cellulolytic activity described below.

The presence of three separate proteins (enzymes) with cellulose-digesting activity secreted [excreted] during the fermentation of *Bacillus subtilis* 6A-1 is surprising. It is apparent that the presence of three separate enzyme fractions identified in the culture supernatant can have an extraordinary advantage in a wide variety of applications.

The procedure was repeated and the cellulolytic enzymes separated by gel electrophoresis were analyzed at pH 11.12 instead of 6.3. The results may be seen in FIG. 11.

In addition to activity expressed upon CMC, gel electrophoresis experiments were expanded to make use of crystalline, more resistant form of cellulose. Similar experiments were executed determining the activity of various protein fractions' catalytic activity upon Avicel®. The results are expressed graphically in FIGS. 12 and 13.

Preparation and analysis of PAG gel segments for cellulase activity expressed on Avicel® microcrystalline cellulose substrate was performed as follows. *Bacillus subtilis* 6A-1 supernatant was run on an 8.0% native polyacrylamide gel electrophoresis (PAGE) gel was prepared for alkaline proteins (as specified in de Lourdes, et. al., p 102). Three wells of the gel were loaded with dialyzed *Bacillus subtilis* 6A-1 enzyme-containing supernatant and were subjected to electrophoresis at 120 V for 4.0 hours using a β-alanine acetic acid mixture as running buffer. The β-alanine acetic acid mixture consisted of 31.2 g of β-alanine, 8 mL of glacial acetic acid and an amount of distilled water sufficient to bring final volume to 1.0 L After the period of electrophoresis, the gel was sliced into 5 mm segments and each segment was placed in separate tubes containing 1 mL of 0.1 M potassium phosphate buffer at pH 7.0. The proteins were allowed to elute into the buffer solution for 48 hours at 4° C. One mL of gel segment elutant was added to 4 mL of the appropriate pH buffer pH 6 and pH 12 (pH 6 buffer prepared by mixing 36.85 mL of 0.1 M citric acid and 63.15 mL 0.2 M $Na_2HPO_4$ then solution titrated with 1M HCl to pH 6.0. pH 12 buffer was prepared by mixing 25 mL of 0.2 M KCl and 6.0 of 0.2 M NaOH then diluted with water to a volume of 100 mL, then solution titrated to pH 12.0) along with 0.10 g of Avicel® microcrystalline cellulose while chilling in an ice bath. The reactant mixtures were incubated with agitation at 40° C. for 1 hour. The reacting mixture was chilled in a 0° C. ice bath and filtered through a 0.45 micron filter. After incubation 800 ul of digestion mix was then added to 1.2 ml of DNS. Tubes were subjected to a boiling water bath for 10.0 min after which they were immersed in an ice water bath and 2.0 mL of deionized water was added to each tube. The absorbance of the each sample was read in spectrophotometer at 540 nm wavelength. One unit of cellulase or amylase activity (DNS method) is defined as the quantity of enzyme that liberates 1.0 micromole of reducing sugar (expressed as glucose equivalents) per minute under the standard conditions of the assay described. The absorbance value for each enzyme-containing sample was calculated by subtracting the enzyme blank value from the enzyme sample value. The net value was used to calculate the activity value from the standard glucose curve.

$$\text{Activity(Enzyme activity/gram)} = \frac{[\text{Activity value from standard curve} \times \text{dilution}]}{[\text{Micromoles glucose} \times \text{reaction time}]}$$

Gel electrophoresis separation of enzymatically active proteins expressed by *Bacillus subtilis* 6A-1 likewise confirm multiple groupings of activity on Avicel®. These data indicate that 6A-1 expresses multiple cellulase enzymes with hydrolytic activity not only on modified cellulose like CMC, but also on crystalline cellulose (Avicel®). The activity of some of the enzyme fractions appear to be active at pH 6.3 and at pH 11.12, while other(s) are predominantly active at pH 11.12.

Therefore, electrophoresis experiments (FIGS. 10, 11, 12 and 13) confirm that there is appreciable cellulase activity by more than one cellulase fraction of *Bacillus subtilis* 6A-1 and these enzyme fractions are active over the broadest of ranges in environmental pH values.

Furthermore, the sum of the data that proves the presence of more than one active cellulolytic enzyme plus the data that indicates that this catalytic activity which elicits hydrolysis of modified cellulose (like CMC), and on chemically unmodified crystalline cellulose (like Avicel®), plus the data that shows the activity extends over a very broad pH spectrum is extraordinary. These attributes provide value for *Bacillus subtilis* 6A-1 and its enzymes as they may be applied to food, feed, biochemical processes and environmental processes. Furthermore, researchers have noted a synergistic hydrolytic action on cellulose substrate when multiple cellulolytic enzymes are applied (Medve, et al— Medve J, Karlsson J, Lee D, Tjerneld F: Hydrolysis of microcrystalline cellulose by cellobiohydrolase I and endoglucanase II from *Trichoderma reesei*: adsorption, sugar production pattern, and synergism of the enzymes. *Biotechnol Bioeng*. 1998, 59: 621-634.). Therefore, *Bacillus subtilis* 6A-1 enzyme preparations offer a unique and distinct advantage.

Example 10

Protease Assessment of *Bacillus subtilis* 6A-1

Prepare the following buffer solutions.

| | Table of Buffer Solutions |
|---|---|
| pH 2 | Citric Acid-$Na_2$ $HPO_4$ Preparation: Mixed 89.1 mL of 0.1M Citric Acid and 10.90 mL of 0.2M $Na_2$ $HPO_4$ then solution titrated with 1M HCl to pH 2.0 |
| pH 4 | Citric Acid-$Na_2$ $HPO_4$ Preparation: Mixed 61.45 mL of 0.1M Citric Acid and 38.55 mL of 0.2M $Na_2$ $HPO_4$ then solution titrated with 1M HCl to pH 4.0 |
| pH 6 | Citric Acid-$Na_2$ $HPO_4$ Preparation: Mixed 36.85 mL of 0.1M Citric Acid and 63.15 mL 0.2M $Na_2$ $HPO_4$ then solution titrated with 1M HCl to pH 6.0 |
| pH 8 | $Na_2$ $HPO_4$—$NaH_2PO_4$ Preparation: Mixed 47.35 mL of 0.2M $NaH_2PO_4$ and 2.65 mL of 0.2M $Na_2$ $HPO_4$ then solution titrated with 1M HCl to pH 8.0 |
| pH 10 | $Na_2CO_3$—$NaHCO_3$ Preparation: Mixed 60 mL of 0.1M $Na_2CO_3$ and 40 mL 0.1M $NaHCO_3$ then solution titrated to pH 10.0 |
| pH 12 | KCl—NaOH Preparation: Mixed 25 mL of 0.2M KCl and 6.0 of 0.2M NaOH then diluted with water to a volume of 100 mL. Rechecked pH. |
| pH 13 | KCl—NaOH Preparation: Mixed 25 mL of 0.2M KCl and 66 mL of 0.2M NaOH then diluted with water to a volume of 100 mL. Rechecked pH. |

The experiment was completed with the following protocol. Combined 200 ul of 2% azocasein in sodium bicarbonate buffer at pH of 8.3 with 200 ul of the buffer needed to produce the required pH, and 100 ul of the *Bacillus subtilis* 6A-1 supernatant. Prepared a standard curve using neutral protease (BioCat) at 0, 20, 40, 60, 80, 100 protease units. Mixed vigorously and incubated the tube at 37° C. for 10 minutes. Placed tubes in icy cold water and added 500 ul of 20% trichloroacetic acid. Vortexed vigorously for 5 minutes. Centrifuged at 10000 rpm for 5 minutes at 4° C. Added 500 ul of supernatant to 1 ml of 1 M NaOH and read the absorbance at 440 nm. Plotted the standard curve readings on a line graph and calculated the slope and intercept of the line produced. Utilized this line to determine the number of protease units/ul/min of the *Bacillus subtilis* 6A-1 supernatant.

Figure 14:
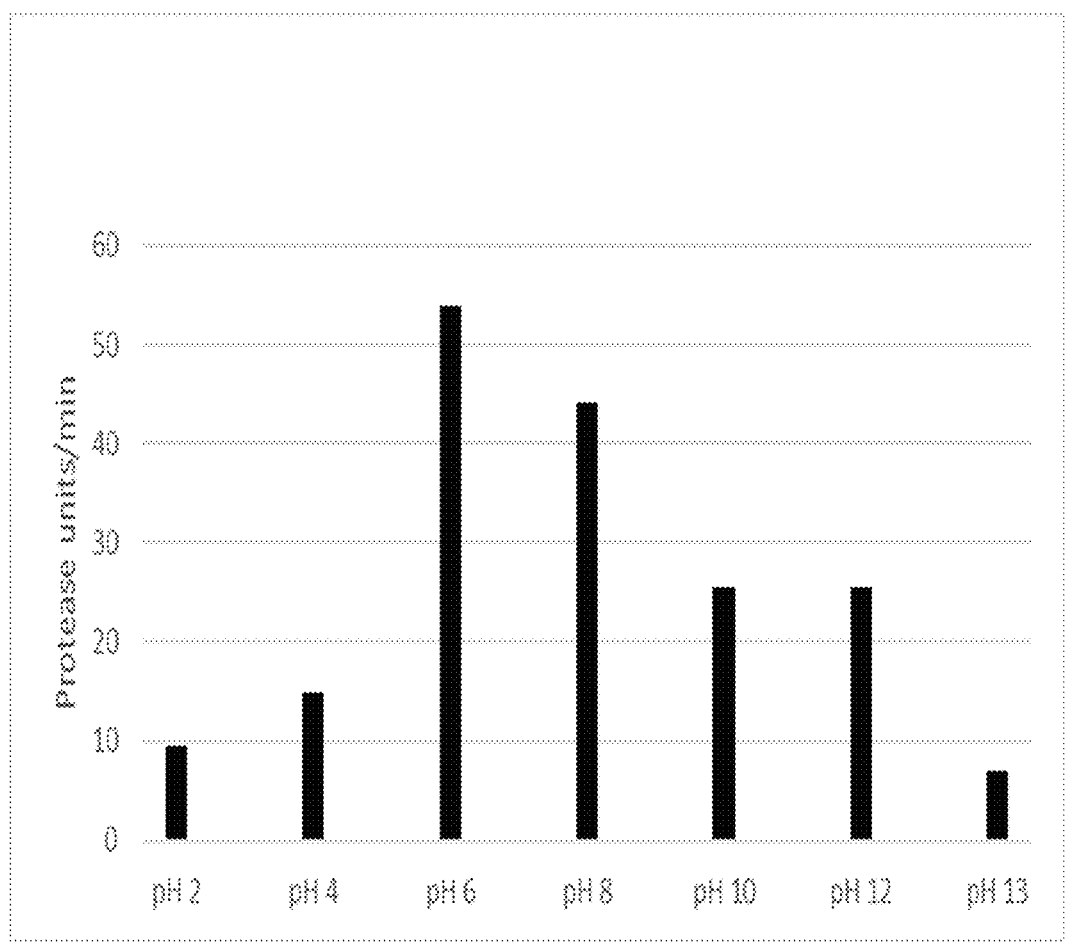
FIG. 14 is a graph showing protease activity of *Bacillus subtilis* 6A-1 supernatant at various pH levels.

The results of this experiment (FIG. 14) indicate that like carbohydrase activity *Bacillus subtilis* 6A-1 has significant protease activity at a wide range of pH levels. The particularly high activity level across pH 6 to pH 12 is especially useful in animal feed and food since it remains active in the varying pH of an animal's digestive system, and is also where used in a detergent.

Example 11

Ensilage Trials Measuring the Effect of *Bacillus subtilis* 6A-1 vs Untreated Control on Ryegrass and Alfalfa The ensilage fermentation process requires crops, grasses, legumes, and other vegetative matter to be enclosed in a relatively airtight or oxygen limiting environment. Prior to that enclosure the materials ensiled may be chopped or ground to expose surfaces of the matter and to assist in proper packing of the material. During time of the enclosure of the material, the ideal ensilage processes progresses as organic acid producing bacteria metabolize available sugars into organic acids and some alcohols (desirably lactic acid, acetic acid, and propionic acid). Organic acid development causes the pH of the ensiled material to be reduced. Preserved storage of the ensilage is possible when the pH of the material is reduced from an original pH of 6.0-7.0 to pH 4.5 or less. In order to achieve the low pH value necessary for proper storage in the quickest possible time, ensiled crops can benefit from the addition of certain enzymes, and viable bacteria (inoculants).

During the research with *Bacillus subtilis* 6A-1, it was discovered that ensiled materials can be treated beneficially from the application of the viable *Bacillus subtilis* 6A-1 (or its viable spores); by the *Bacillus subtilis* 6A-1-produced cellulolytic enzymes; or by combination of the viable *Bacillus* spp. along with its enzymes.

By inoculating ensiled materials with viable *Bacillus subtilis* 6A-1 and/or its enzymes, a more optimal preservation state may be reached. In addition, the resultant silage may contain higher level of organic fatty acids which have positive effect on butterfat production by lactating dairy cows.

The data in the Table 1 below represents a compilation of experimental data from trials in year 1 and year 2 performed upon ensiled ryegrass. Both *Bacillus subtilis* 6A-1 viable cells/spores and *Bacillus subtilis* 6A-1 enzyme containing broth extract were used to treat the ryegrass silage. Ryegrass is a forage crop that is particularly difficult to ensile commonly due to its high moisture content and possibly the low content of fermentable sugars in overly matured stage of growth. It is very important that pH levels in the ensiled crop drops rapidly to a low level to ensure optimal storage condition. Procedures for the experimental process are found below, along with an interpretation of the data. TMT refers to Total Mixed Ration (60% Corn, 25% SBM (Soy Bean Meal).

TABLE 1

Ryegrass Ensilage Trials

| TMT | % Lactic acid | % Acetic Acid | % Mannitol | pH |
|---|---|---|---|---|
| Control[3] | 11.21 | 2.91$^a$ | 1.93$^a$ | 3.96$^a$ |
| 6A-1[3] | 11.01 | 2.51$^b$ | 2.77$^b$ | 3.76$^b$ |
| Control[4] | 10.66 | 2.24a | 0.08$^a$ | 4.22 |
| 6A-1 extract[4] | 10.88 | 1.79b | 0.23$^b$ | 4.19 |

| TMT | % DM[1] loss | % DMD[2] 8 h | Ammonia-N$_{ppm}$ | Yeast* |
|---|---|---|---|---|
| Control[3] | 3.74$^a$ | 35.39$^a$ | 3064$^a$ | 251$^a$ |
| 6A-1[3] | 2.69$^b$ | 39.25$^b$ | 2904$^b$ | 33$^b$ |
| Control[4] | 2.55 | 55.29 | 3235 | 20893$^a$ |
| 6A-1 extract[4] | 2.44 | 56.37 | 3051 | 3388$^b$ |

Superscript a and b values represent data points which vary by statistically significant amount ($P < 0.05$).
[1]Dry Matter Loss (DM Loss) is a measure of the loss of dry weight of the ensiled material lost during the ensiling fermentation. See definition below.
[2]DMD (Dry Matter Digestibility or Dry Matter Disappearance) is a measure of the resultant digestibility of the feedstuffs in the animal or under animal-like conditions. The DMD is measured by taking a standard quantity of the dried substrate, placing it in the solution according to the procedure described below that aids in the digestion of feedstuffs. See definition below.
[3]Year 1
[4]Year 2
*Represents yeast count in CFU/g-.

In year 1, *Bacillus subtilis* 6A-1 viable bacteria only were used to treat ensiled crop to determine effects of *Bacillus subtilis* 6A-1 as a silage inoculant. Viable cells of 6A-1 were dosed at approximately 100,000 cfu/g (Colony Forming Units/gram) of the forage which was treated. In year 2, *Bacillus subtilis* 6A-1 enzyme broth was separated from the viable *Bacillus subtilis* 6A-1 viable cells and spores by filtration with 0.45 μm filter, and this process yielded a bacteria-free broth extract at an estimated enzymatic concentration described as follows: 68 ml of 6A-1 broth with an activity level of 0.4 DNS enzyme units per ml was added into 30 pounds of chopped ryegrass, mixed and placed into the silos made up of PVC pipe, and the whole contents were weighed and recorded as initial weight. The contents were allowed to ferment for 33 days. After 33 days, silos were weighed and the Dry Matter (DM) loss percentage was calculated for each silo by determining the difference between the initial and final weight of the silos and dividing that by the initial weight and multiplying by 100. Silos were opened and representative portions representing approximately 300 grams (as sampled basis) of the fermented forage were obtained and processed for the following values: pH, % Volatile Fatty Acids (VFA) by Capillary Electrophoresis. Capillary Electrophoresis (CE) is an analytical tool which permits rapid and efficient separations of charged organic acid components present in small sample volumes. Clean separations of these organic acids are based on the differences in electrophoretic motilities of ions in electrophoretic media inside small capillaries. In year 1, ryegrass was harvested at high moisture and ensiled the same day. In year 2, the ryegrass was allowed to wilt for 24 hours.

An 8 hour in vitro Dry Matter Digestibility (DMD) was performed on the samples by placing 1.0 g of sample combined with DMD solution (Solution A: $CaCl_2$ $2H_2O$ 0.1 g/L, $MgSO_4$ $7H_2O$ 0.5 g/L, NaCl 0.5 g/L, Urea 0.5 g/L and $KH_2PO_4$ 10 g/L and Solution B:$Na_2S$ $9H_2O$ 0.4 g/L, $Na_2CO_3$ 6.0 g/L). The following protocol was used in the experiment. Solution B was added to Solution A until pH of 6.8 is reached). This mixture was allowed to incubate for 8 hours at 39° C. The contents were filtered through a very finely porous glass crucible, the residual material was washed several times with distilled or deionized water, and the residual content was dried at 100° C. for 6 hours. The difference between the original dry weight and the residual dry weight divided by the original dry weight multiplied by 100 is considered as the percentage of dry matter disappeared or Digestible Dry Matter (DMD). The higher the DMD, the higher the percentage of nutrients that may be "digestible" or available to animals; higher DMD results in positive production conditions.

Other analytical procedures were performed to assess the performance of silage treatments, Ammonia-N(Ammonia Nitrogen concentration), Mannitol [% concentration] and Yeast Viable Count-CFU/g (CFU/g was measured on an as-sampled basis).

The data in Table 1 shows a definite improvement in ryegrass silage (often called ryelage or haylage) treated with 6A-1 over the untreated control lot of silage. The positive effects were somewhat more noticeable in year 1 than in year 2. More acetate (acetic acid) produced during an ensilage fermentation is indicative of a more heterofermentation (fermentation by heterofermentative lactic acid-forming bacteria), rather than a homofermentation which is usually judged to yield silage of higher nutritional quality. A heterofermentation could lead to more inefficient energy conservation due to loss of more $CO_2$ during the ensilage fermentation ($CO_2$ loss accompanies production of acetic acid). Acetic acid or acetate may actually be good for silage bunk life, but excessive concentration in the silage is detrimental to silage intake by ruminants. There was significantly less acetic acid formed during the ryegrass fermentation when Bacillus subtilis 6A-1 viable cells or 6A-1 enzyme-containing broth was added at time of ensiling.

It is always positive to have a lower pH level at the end of grass or hay-type ensilage fermentation since lower pH levels will prevent spoilage caused by yeast and mold, There were lower pH levels attained with both 6A-1 treatments of the silage; statistically the pH was lowered significantly when viable Bacillus subtilis 6A-1 was added to the ensilage as an inoculant.

The Bacillus subtilis 6A-1 viable cells significantly depressed viable yeast content in the finished silage for the year 1 (this is a great advantage for silage stability).

Ammonia concentrations were numerically lower in both years with both 6A-1 treatment types (significantly so for year 1 when the viable 6A-1 was used as a viable inoculant). These results indicate that 6A-1 prevented conversion of plant protein into inefficient and potentially toxic ammonia. Ammonia is the result of breakdown of amino acids in proteins releasing the ammonium moiety. Protein conservation during the ensilage fermentation is essential for preserving and yielding a high nutritional quality end product.

There were increases in in vitro Dry Matter Digestibilities (DMD) both years in the 6A-1 treated haylage. It is likely that 6A-1 enzymes pre-digest nutrients while the ensiling process continues. Analysis to determine Dry Matter Loss indicated that the 6A-1 treated silos in both years of experimentation experience less loss of dry matter during the ensiling process.

An alfalfa ensiling trial was executed in the same manner as described above, except that the forage used in the trial was alfalfa instead of ryegrass and Bacillus subtilis 6A-1 enzyme broth separated from viable cells was used as above. Alfalfa represents a particularly valuable forage crop, having high protein content. However, alfalfa is also typically difficult to ensile in optimal manner. The buffering capability of the plant contents, and low fermentable sugars found in the crop result in silages which have only moderately reduced pH and relatively low content of lactic acid. This phenomenon results in the potential deterioration of alfalfa silages and unsatisfactory stability under typical storage conditions. Treatment of alfalfa with Bacillus subtilis 6A-1 using dry inoculant at the rate of 2 DNS units/kilogram of silage, as in the ensiling trial describe above, resulted in statistically better quality resultant silage. These results are reported in the table below:

TABLE 2

| | Alfalfa Ensiling Trial | | | | |
|---|---|---|---|---|---|
| TMT | Initial pH | Final pH | Initial % Lactic Acid | Final % Lactic Acid | % Dry Matter Loss |
| Control | 5.92 | $4.333^a$ | 0.127 | $4.95^a$ | $0.872^a$ |
| 6A-1 Treated | 5.92 | $4.223^b$ | 0.127 | $6.94^b$ | $0.840^b$ |

Superscripts $a$ and $b$ beside values indicate that the values are statistically different from one another.

Viable Bacillus subtilis 6A-1, when used as an inoculant, as well as the 6A-1 enzyme treatment reduced Dry Matter loss normally experienced during ensilage fermentations. Conservation of dry matter during the ensiling process is a measure of the efficiency of the fermentative ensiling process and increased Dry Matter conservation during ensiling represents a great economic benefit to farmers because it means lower feed cost and less wastage of nutrients.

In summary, the treatment of ensiled crops either with viable Bacillus subtilis 6A-1 or with Bacillus subtilis 6A-1 enzymes at time of ensiling results in a higher quality silage at the completion of fermentation. At the end of fermentation the pH of the environment increases to the point the bacteria cannot survive.

Example 12

In Vitro and In Vivo Studies of Effects of Bacillus subtilis 6A-1 on Rumen Digestion To determine the effects of directly feeding Bacillus subtilis 6A-1 to ruminants, an in vitro digestibility study of ruminant ration and ration components with and without *Bacillus subtilis* 6A-1 viable cells and/or enzymes was performed. *Bacillus subtilis* 6A-1 cells and spores were separated from the strain's enzymes by standard techniques of centrifugation or centrifugation followed by filtration through a 0.45 micron filter. The enzyme-containing liquid from the bacterial fermentation forms the supernatant which can be decanted achieving separation from *Bacillus subtilis* 6A-1 cells and spores. Filtration further refines the enzyme extract. This separation technique is offered as example only. Enzyme separation and purification and even concentration may be accomplished by other known technologies including but not limited to: simple membrane filtration, ultrafiltration, tangential flow technique, differential precipitation, and others.

The enzyme extract was added to an in vitro continuously operating rumen apparatus. This apparatus has been shown to mimic results obtained from addition of ingredients, and additives in vivo (in fistulated and unfistulated ruminating cattle). Digestion of fiber was enabled to higher degree in the in vitro rumen as well. Positive effects in vitro are translated into achieving more efficient feed digestion in ruminants. A *Bacillus subtilis* 6A-1 preparation produced for optimal enzyme production was added to similar apparatus along with the enzymes it produced.

Table 3 and 4 represent a compilation of data obtained from in vitro digestibility utilizing a series of 0.25 gram samples of Corn Silage, TMR, and Hay samples were placed into in vitro tubes containing buffer at pH 6.5. TMR refers to Total Mixed Ration and the components of the ration vary depending upon the animal that will be fed and the crops and feed available. Composition of the TMR here used is described below. Approximately 20 μL of *Bacillus subtilis* 6A-1 broth was added to each tube and the tubes containing the buffer previously described were incubated at 39.5° C. for 16 hours to measure any improvements in digestibility of given feedstuffs obtained with the addition of *Bacillus subtilis* 6A-1 fermentation products (broth, viable cells, and/or enzyme containing broth extract) versus digestibilities noted with untreated control samples. The liquid *Bacillus subtilis* 6A-1 culture was added at a comparative rate of 80 mL/head/day. In every trial *Bacillus subtilis* 6A-1 fermentation products elicited an improvement in digestibility over the untreated lots. These data indicate that the use of *Bacillus subtilis* 6A-1 in ruminant livestock diets can be expected to improve digestibility of representative rations and feedstuffs fed the animal. Increasing efficiency of digestibility is directly related to improving economic value in feeding livestock.

TABLE 3

In Vitro Digestibility[1] of Ruminant Ration and Ration Components With and Without *Bacillus subtilis* 6A-1 Viable Cells and/or Enzymes

| Type of Sample | Hours of Incubation | Control No 6A-1 | 6A-1 Broth | 6A-1 Viable Cells | 6A-1 Enzymes |
|---|---|---|---|---|---|
| Corn Silage 1 | 24 | 60.8 | 67.36 | | |
| Corn Silage 2 | 12 | 55.08 | | 56.32 | |
| Corn Silage 3 | 24 | 64.89 | | 66.8 | |
| Hay | 16 | 55.2 | | | 56.71 |
| Total Mixed Ration[2] (TMR) | 16 | 56.56 | | 58.2 | 59.24 |

[1]All Digestibility values are in %. The difference between the final and initial weight of the TMR sample divided by the initial weight and multiplied by 100 yielded the digestibility values.
[2]The composition of the TMR was follows: 60% CS, 15% Alfalfa Haylage, 15% Corn, and 10% SBM)

Volatile Fatty Acid (VFA) development in the rumen of livestock is an indicator of the manner in which the hydrolyzed sugars are fermented so as to enable them to be absorbed for efficient animal assimilation. Furthermore, there is a positive relationship between VFA development, energy produced from a fed animal ration, and in lactating cattle, the butterfat produced in milk yielded. The total VFA values measured for 6A-1 treatments showed an appreciably increased value for total VFA produced over the Control. Expressed on an as-is basis, the 6A-1 group of treatments show increases in total VFA development from the rations.

All of these factors are positive, and indicate that the addition of *Bacillus subtilis* 6A-1 can have positive nutritional effects on the digestion of feedstuffs in ruminants.

TABLE 4

In Vitro Analysis[1] of Ruminant Rations for Volatile Fatty Acid Development With and Without Treatment with *Bacillus subtilis* 6A-1 Viable Cell and Enzyme

| Type of Sample | VFA[2] Types | Control No 6A-1[3] | 6A-1 Viable Cells | 6A-1 Enzymes |
|---|---|---|---|---|
| Hay | Acetate | 57.34 | 57.91 | 57.57 |
| | Propionate | 25.66 | 24.72 | 24.64 |
| | Sum VFA (μM/mL) | 51.43 | 69.2 | 73.2 |
| Total Mixed Ration[4] (TMR) | Acetate | 54.54 | 55.99 | 53.14 |
| | Propionate | 31.66 | 30.9 | 31.58 |
| | Sum VFA (μM/mL) | 51.96 | 59.54 | 60.62 |

[1]See procedure for in vitro analysis and VFA analysis: IVDMD, Tilley, J. M. A. and R. A. Terry. 1963. A two stage technique for the in vitro digestion of forage crops. *J. Brit. Grassl. Soc.* 8: 104. For VFA, Erwin, E. S., G. J. Marco and E. M. Emory. 1961. Volatile fatty acid analysis of blood and rumen fluid by gas chromatography. *J. Dairy Sci.* 44: 1768
[2]VFA = Volatile Fatty Acid
[3]All VFA values are in moles/100 mL
[4]The composition of the TMR was as follows: 60% CS, 15% Alfalfa Haylage, 15% Corn, and 10% SBM)

The effect of *Bacillus subtilis* 6A-1 on ruminant and swine rations were assessed in the following manner. A 1.0 gram sample of the Total Mixed Ration (60% Corn, 25% SBM (Soy Bean Meal) and 10% DDG (Dried Distiller's Grains)) was incubated at 39.5° C. with 120 mL of each buffer (buffer solutions found in Enzyme Activity in Polysaccharides) at the recorded pH, and 0.1 g of *Bacillus subtilis* 6A-1 culture produced upon semi-solid substrate was added. Incubation of the enzyme-bearing culture of *Bacillus subtilis* 6A-1 with the rations specified was arrested after 60 minutes by immersion in a 0° C. ice bath. The sample was filtered through 0.45 micron filter and the filtered liquid was subjected to cellulase activity assay (found in Cellulase and Amylase enzyme Activity Determination) to measure the sugars liberated from the rations.

Figure 15:
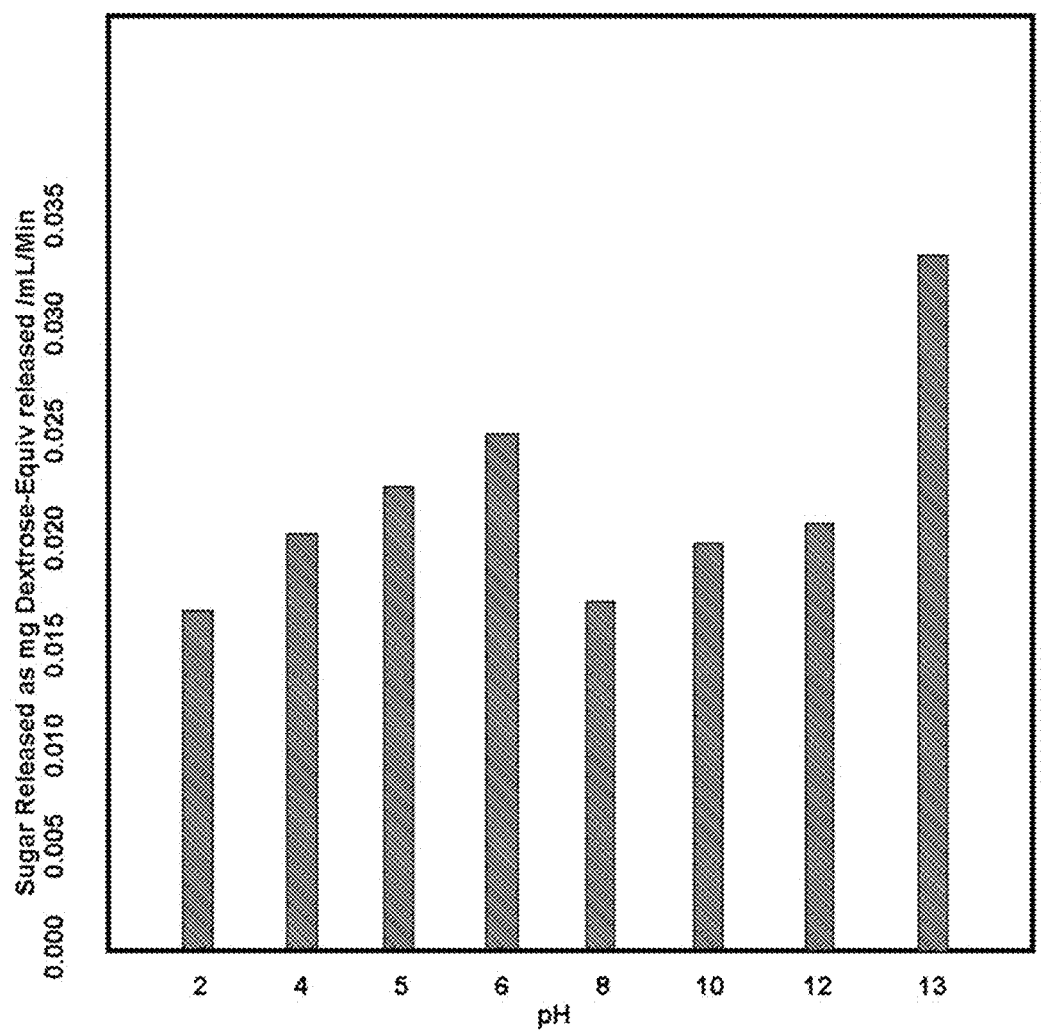
FIG. 15 is a graph showing sugars released from Dried Distillers Grain based swine ration as a result of treatment with 50 μL of *Bacillus subtilis* 6A-1 enzyme-containing broth.

The information in FIG. 15 is from incubating *Bacillus subtilis* 6A-1 enzyme containing broth at 50 μL level with Swine-type diet containing 60% Corn, 25% SBM (Soy Bean Meal) and 10% DDG (Dried Distiller's Grains). These results indicate that 6A-1 is effective in digesting a typical swine-type ration over the very broad pH range of 2-13.

Figure 16:
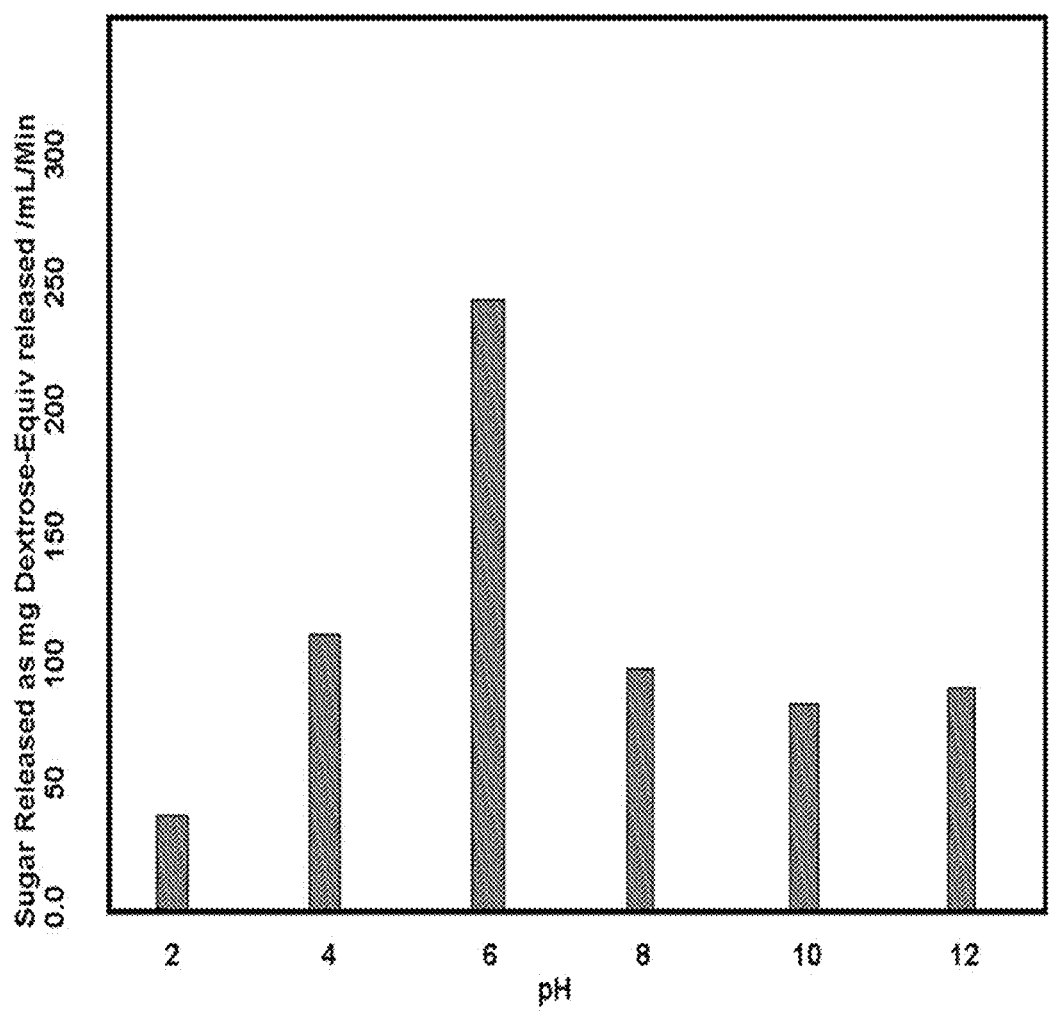
FIG. 16 is a graph showing sugars released from Total Mixed Ration—fed ruminants as a result of treatment with *Bacillus subtilis* 6A-1 enzyme-containing SSWM at various pH levels.

The FIG. 16 represents the use of *Bacillus subtilis* 6A-1 enzyme-containing fermentation product, produced by semi-solid culturing method. The method for production is described below. The enzyme-containing material was added to a ration suitable for a ruminant type diet. A total mixed ration (TMR) was utilized. This typical TMR contained corn silage, alfalfa haylage, ground corn and mineral supplement. These results indicate that 6A-1 is effective in digesting a typical ruminant-type ration over the very broad pH range of 3-12.

Semi-solid fermentation production of *Bacillus subtilis* 6A-1 enzyme and viable cell containing fermentation product was produced in the following manner. 800 ml of distilled water was added to 1000 g of Wheat Bran (from Bob's Red Mill) along with 200 ml of 0.1 M potassium pH 7.0 phosphate buffer. In the liquid addition was suspended or dissolved: 20 g $CaCO_3$, 41 g $CaCl_2$ dihydrate and 6.29 g $MnCl_2*4H_2O$. The moistened bran mixture was spread into 9×13 inch trays and covered with aluminum foil. The trays were autoclaved for 15 min at 121° C. and 15 psi.

The semi-solid medium so prepared was cooled to less than 40° C. and was inoculated with 35 ml of vegetative *Bacillus subtilis* 6A-1 broth (prepared as above) and incubated at 37° C. for 24 hours. The semi-solid fermentation product thus prepared was then dried 18 hours at 54° C. to less than 15% moisture. The resulting dry material was utilized in the animal feeding trial and in results reported as semi-solid wheat media or SSWM.

Dry semi-solid product of *Bacillus subtilis* 6A-1 (SSWM) was rehydrated (1 g in 50 ml of distilled $H_2O$) and held at room temperature for 10 min. The rehydrated mixture was filtered using 3 layers of cheesecloth then the filtrate was further filtered through a 0.45μ filter. The 6A-1 aqueous extract was then used in studies which specify the use of *Bacillus subtilis* 6A-1 semi-solid material either in dry granular form or in aqueous extracted form.

In vitro research has been supported by in vivo feeding trials which further prove the efficacy of *Bacillus subtilis* 6A-1 addition to diets of livestock. In the table below data is reported for the dry matter digestibility (DMD) from a trial using 12 lambs per treatment averaging 28 pounds each in weight. All groups were fed a Total Mixed Ration (TMR) composed of corn silage, haylage, and minerals/vitamin supplement. The animals were placed in collection crates for a 3 day adjustment period prior to the beginning of the trial. All animals had been exposed to the basal TMR diet used for more than 30 days.

Approximately, 1.0 gram of *Bacillus subtilis* 6A-1 produced by the semi-solid production method described above was fed after the mixture was ground through 4 mm screen to allow homogeneous sampling of the 6A-1 preparation. The 1.0 gram of 6A-1 preparation was mixed into the TMR thoroughly, and specific amounts were fed twice a day to each animal. All animals were fed ad libitum to prevent any limitation that may skew natural intake tendencies.

Feed, feed refusals and fecal samples were collected during the five day collection. Samples were frozen until the end of trial, then analyzed. The amount of feed (wet weight) fed, the feed refused and the amount of wet fecal weights were recorded daily during the collection period, and these weights were converted to dry weights after determining the dry matter contents of each sample.

Analysis of the residual waste from the sheep-fed trial was performed and compared to quantitative amounts of original ration ingested during the trial described above. The feeding trial yielded data which is reported in the table below (all values stated are in %):

TABLE 5

Residual Waste Analysis of In Vivo Sheep fed *Bacillus subtilis* 6A-1

| | Dry Matter (in vivo)[1] Digestibility | Neutral Det. Fiber[2] Digestibility | ADF[3] Digestibility | Hemicellulose[4] Digestibility |
|---|---|---|---|---|
| Control | 65.3 | 40.4 | 36.1 | 46.43 |
| 6A-1 Treated | 66.19 | 44.29 | 40.99 | 48.99 |

[1]The percent Dry Matter Digestibility (DMD) in vivo was calculated by subtracting from Total Dry Feed fed/day the total dry feed refused (which was the Actual Feed Intake) minus total dry fecal weights. The value obtained was divided by the Actual Feed Intake multiplied by 100.
[2]The percentage Neutral Detergent Fiber (NDF) Digestibility was determined by comparing ingested feed with analysis of the manure collected in similar fashion to that calculation for Total Dry Matter Digestibility reported above (In determining NDF values, a neutral detergent solution is used to dissolve the easily digested pectins and plant cell contents (proteins, sugars, and lipids); leaving a fibrous residue (aNDF) that is primarily cell wall components of plants (cellulose, hemicellulose, and lignin). Detergent is used to solubilize the proteins and sodium sulfite also helps remove some nitrogenous matter; EDTA is used to chelate calcium and remove pectins at boiling temperatures; triethylene glycol helps to remove some non-fibrous matter from concentrate feeds; and heat-stable amylase is used to remove starch. Two additions of amylase (one during refluxing and one during filtration) have been observed to aid NDF analyses and minimize filtering difficulties. Heat-stable amylases are used in hot solutions to inactivate potential contaminating enzymes that might degrade fibrous constituents (AOAC Official Method 2002.04 Amylase-Treated Neutral Detergent Fiber in Feeds). NDF is the most common measure of fiber used for animal feed analysis, but it does not represent a unique class of chemical compounds. NDF measures most of the structural components in plant cells (e.g. lignin, hemicellulose and cellulose).
[3]The percentage Acid Detergent Fiber (ADF) Digestibility was determined by comparing ingested feed with the analysis of the manure collected in similar fashion to that calculation for Total Dry Matter Digestibility reported above. Values for ADF were determined by the ADF methodology outlined above.
[4]The percentage Hemicellulose Digestibility was determined by comparing ingested feed with the analysis of the manure collected in similar fashion to that calculation for Total Dry Matter Digestibility reported above. Hemicellulose content is defined as the residue extracted when an NDF residue is subjected to boiling Acid Detergent Solution (as specified in the ADF procedure) for one hour. (% NDF − % ADF = % Hemicellulose)

Higher comparative DMD values in a feeding trial with variations in feed would describe a situation where the test animal(s) are able to digest and assimilate feed to a comparatively greater degree. Thus comparatively higher DMD values in a feeding trial are desirable and indicate that a feed composition has higher degree of feeding value. DMD for the treated feed was appreciably higher than for the Control feeds. This provides for more efficient feeding for the livestock producer who uses *Bacillus subtilis* 6A-1 preparations mixed in feed.

In a livestock feeding program, efforts are made to increase the Dry Matter Digestibility of feed, and more recently greater efforts are concentrated in achieving better digestibility of the fiber portions of the feed such as NDF, ADF, and Hemicellulose. The higher the values, the better the efficiency of dry matter intake, healthy rumen functions with ruminants, and optimized milk components such as percent milk butter fat and percent milk proteins.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10138444B2). An electronic copy of the "Sequence Listing" will also be available from the USPTO upon request and payment of the fee set forth in 37 CFR 1.19(b)(3).

What is claimed is:

1. A method of producing a composition capable of degrading at least one polysaccharide, the method comprising,
   a) culturing strain *Bacillus subtilis* 6A-1 (6A-1), reference culture comprising said 6A-1 having been deposited at ATCC under deposit number PTA-125135, such that said 6A-1 produces at least two polysaccharide-degrading protein fractions;
   b) a process selected from (i) filtering or drying or freeze drying or grinding, or adding at least one excipient, carrier or diluent to said 6A-1 strain or cells or spores of said 6A-1 or (ii) extracting at least one polysaccharide-degrading protein fraction from said 6A-1, or iii) a combination thereof and
   c) producing a composition comprising said strain, cells, spores or at least one polysaccharide-degrading protein fraction extraction of b), or a combination thereof.

2. The method of claim 1, wherein said composition comprises at least three cellulose-degrading protein fractions produced by said 6A-1, said protein fractions capable of degrading crystalline cellulose, carboxymethyl cellulose and unmodified cellulose.

3. The method of claim 1, wherein said composition is capable of degrading protein at a pH of 2 to 12.

4. The method of claim 1, wherein said 6A-1 is an asporogenous mutant of said 6A-1.

5. The method of claim 1, wherein said composition is capable of degrading cellulose under conditions from pH 2 to pH 13.

6. The method of claim 1, wherein said composition is capable of degrading acid detergent fiber.

7. The method of claim 1, wherein said 6A-1 is cultured at a temperature of less than 55° C.

8. The method of claim 1, wherein said 6A-1 is cultured at a temperature of 30°-35° C.

9. The method of claim 1, wherein said 6A-1 is cultured in a liquid or semi-solid medium.

10. A method of producing an edible composition for an animal, the method comprising,
    a) culturing strain *Bacillus subtilis* 6A-1 (6A-1), reference culture comprising said 6A-1 having been deposited at ATCC under deposit number PTA-125135 such that said 6A-1 produces at least two polysaccharide-degrading protein fractions;
    b) a process selected from (i) filtering or drying or freeze drying or grinding, or adding at least one excipient, carrier or diluent to said 6A-1 strain or cells or spores of said 6A-1 or (ii) extracting at least one polysaccharide-degrading protein fraction from said 6A-1, or iii) a combination thereof; and
    c) producing an edible composition selected from
       (i) a composition comprising said strain, cells, spores or at least one polysaccharide-degrading protein fraction or combination thereof of b); or
       (ii) a composition comprising one or more plants or plant parts fermented with said strain, cells spores or at least one polysaccharide-degrading protein fraction or combination thereof of b) until said fermentation is complete.

11. The method of claim 10, wherein b) comprises drying said 6A-1 strain, cells, spores or at least one polysaccharide-degrading protein fraction or combination thereof and further comprises spraying said dried strain cells, spores or at least one polysaccharide-degrading protein fraction or combination thereof onto one or more plants or plant parts.

12. The method of claim 10, comprising producing a probiotic edible composition comprising said strain, cells, spores or at least one polysaccharide-degrading protein fraction or combination thereof of b).

13. A method of feeding an animal, the method comprising,
    a) culturing strain *Bacillus subtilis* 6A-1 (6A-1), reference culture comprising said 6A-1 having been deposited at ATCC under deposit number PTA-125135 such that said 6A-1 produces at least two polysaccharide-degrading protein fractions;
    b) a process selected from (i) filtering or drying or freeze drying or grinding, or adding at least one excipient, carrier or diluent to said 6A-1 strain or cells or spores of said 6A-1 or (ii) extracting at least one polysaccharide-degrading protein fraction from said 6A-1, or iii) a combination thereof;
    c) feeding said animal an edible composition selected from,
       (i) said strain, cells, spores or at least one polysaccharide-degrading protein fraction or combination thereof of b); or
       (ii) a composition comprising one or more plants or plant parts fermented with said strain, cells spores or at least one polysaccharide-degrading protein fraction or combination thereof of b) until said fermentation is complete.

14. The method of claim 13, wherein said polysaccharide degrading protein fractions retain said polysaccharide degrading activity at a pH of 2 to 13.

15. The method of claim 13, wherein said animal is selected from a lactating animal, ruminant, lactating ruminant, poultry, swine, equine, canine, feline, or rabbit.

16. The method of claim 13, wherein said edible composition comprises said plants or plant parts.

17. The method of claim 16, wherein dry matter digestibility, neutral detergent digestibility, acid detergent fiber digestibility or hemicellulose digestibility or a combination thereof of said edible composition is increased after said fermentation is complete.

18. The method of claim 16, wherein lactic acid is lower, pH is lower, or ammonia concentration lower, or a combination thereof of said edible composition after said fermentation is complete.

19. The method of claim 1, wherein said strain, cells, spores or at least one polysaccharide-degrading protein fraction is dried or freeze dried.

20. The method of claim 1, wherein said composition comprises said strain.

21. The method of claim 1, wherein said composition comprises said cells or spores.

22. The method of claim 1, wherein said at least one excipient, carrier or diluent is edible.

23. The method of claim 1, wherein said composition is edible.

* * * * *